United States Patent [19]

Sackner et al.

[11] Patent Number: 4,484,577

[45] Date of Patent: Nov. 27, 1984

[54] DRUG DELIVERY METHOD AND INHALATION DEVICE THEREFOR

[75] Inventors: Marvin A. Sackner, Miami Beach; Herman Watson, Miami, both of Fla.

[73] Assignee: Key Pharmaceuticals, Inc., Miami, Fla.

[21] Appl. No.: 377,469

[22] Filed: May 12, 1982

Related U.S. Application Data

[63] Continuation-in-part of Ser. No. 285,992, Jul. 23, 1981, abandoned, which is a continuation of Ser. No. 280,631, Jun. 6, 1981, abandoned, which is a continuation of Ser. No. 142,697, Apr. 22, 1980, abandoned.

[51] Int. Cl.$^3$ .................................................. A61M 15/00
[52] U.S. Cl. .......................... 128/203.28; 128/200.23; 128/203.29
[58] Field of Search ................ 128/200.14, 200.18, 128/200.21, 200.22, 200.23, 200.24, 203.25, 203.28, 203.29, 204.18, 205.13, 205.17, 205.21, 207.14, 207.16, 716, 719, 720, 725, 727, 728, 730; 46/44; 92/34–47, 9; 73/729

[56] References Cited

U.S. PATENT DOCUMENTS

| | | |
|---|---|---|
| 844,449 | 2/1907 | Green . |
| 1,357,601 | 11/1920 | Walter ............................ 128/203.28 |
| 2,007,330 | 7/1935 | Hicks .................................... 128/27 |
| 3,045,671 | 7/1962 | Updegraff ...................... 128/205.21 |
| 3,455,294 | 7/1969 | Adler ..................................... 128/25 |
| 3,473,529 | 10/1969 | Wallace ............................ 128/145.7 |
| 3,507,278 | 4/1970 | Werding ............................... 128/214 |
| 3,635,214 | 1/1972 | Rand .................................... 128/2.08 |
| 3,754,546 | 8/1973 | Cooper ................................ 128/2.08 |
| 3,859,997 | 1/1975 | Douma et al. .................. 128/205.17 |
| 3,861,396 | 1/1975 | Vaillancourt ........................ 128/350 |
| 4,119,097 | 10/1978 | Spector ................................. 128/203 |
| 4,210,155 | 7/1980 | Grimes .................................. 128/727 |
| 4,226,233 | 10/1980 | Kritzer ............................ 128/205.13 |
| 4,241,740 | 12/1980 | Brown ................................... 128/728 |
| 4,291,688 | 9/1981 | Kistler ............................ 128/200.23 |
| 4,291,704 | 9/1981 | Petty et al. .......................... 128/728 |

FOREIGN PATENT DOCUMENTS

| | | |
|---|---|---|
| 2803993 | 8/1978 | Fed. Rep. of Germany . |
| 436569 | 1/1912 | France ................................. 128/728 |

OTHER PUBLICATIONS

The Merck Index, 9th ed. 1976, pp. 30, 542 and 772.
Laros et al., "Absorption, Distribution and Excretion of the Tritium–Labelled $\beta_2$ Stimulator Fenoterol Hydrobromide Following Aerosol Administration and Instillation into the Bronchial Tree", *Respiration*, vol. 131, p. 140, (1977).
Newman et al., "How Should a Pressurized $\beta$-Adrenergic Bronchodilator be Inhaled?", *Eur. J. Respir. Dis.*, vol. 62, pp. 3–21, (1981).

(List continued on next page.)

*Primary Examiner*—Henry J. Recla
*Assistant Examiner*—Karin M. Reichle
*Attorney, Agent, or Firm*—Wegner & Bretschneider

[57] ABSTRACT

A method and an apparatus for administering a drug through a breathing passage for absorption on the mucous tissue of a patient includes introducing an aerosol of the drug into an expanded bag and bidirectional channel for communicating the drug with the breathing passage of the patient and otherwise is substantially impervious to the passage of air, collapsing the expanded bag while the bidirectional channel for communicating with the breathing passage is in position to deliver the drug into the breathing passage of the patient. A signal in a bidirectional channel indicates when the rate of passage of the drug exceeds a desirable limit, whereby the patient taking the drug is reminded to decrease the rate of collapse of the airbag, thereby maximizing drug utilization. The drug delivery device admits a drug-containing aerosol through a drug introduction opening while the collapsible airbag is at least partially expanded, the drug being introduced into the breathing passage with the contraction of the collapsible airbag.

24 Claims, 19 Drawing Figures

OTHER PUBLICATIONS

Heimer et al., "The Effect of Sequential Inhalations of Metaproterenol Aerosol in Asthma", *J. Allergy Clin. Immunol.*, vol. 66, No. 1, pp. 75–77, (1980).

Bell et al., "Variation in Delivery of Isoprenaline from Various Pressurized Inhalers", *J. Pharm. Pharmac.*, vol. 25, Suppl., pp. 32–36, (1973).

Godden et al., "An Ojective Assessment of the Tube Spacer in Patients Unable to Use a Conventional Pressurized Aerosol Efficiently", *Br. J. Dis. Chest*, vol. 75, pp. 165–168, (1981).

Moren, "Drug Deposition of Pressurized Inhalation Aerosols", I. Influence of Actuator Tube Design, *International Journal of Pharmaceutics*, vol. 1, pp. 205–212, (1978).

"The Proper Use of Aerosol Bronchodilators", *The Lancet*, pp. 23–24, Jan. 3, 1981.

Gayrard et al., "Mauvaise Utilisation des Aerosol-Doseurs par les Asthmatiques", *Respiration*, vol. 40, pp. 47–52, (1980).

Gomm et al., "Effect of an Extension Tube on the Bronchodilator Efficacy of Terbutaline Delivered from a Metered Dose Inhaler", *Thorax*, vol. 35, pp. 552–556, (1980).

Popa, "How to Inhale a Whiff of Pressurized Bronchodilator", *Chest*, vol. 76, pp. 496–498, (1979).

Freigang, "New Method of Beclomethasone Aerosol Administration to Children Under 4 Years of Age", *CMA Journal*, vol. 117, pp. 1308–1309, Dec. 3, 1977.

Shim et al., "The Adequacy of Inhalation of Aerosol from Canister Nebulizers", *The American Journal of Medicine*, vol. 69, pp. 891–894, (1980).

Newman et al., "Simple Instructions for Using Pressurized Aerosol Bronchodilators", *Journal of the Royal Society of Medicine*, vol. 73, pp. 776–779, (1980).

Ellul-Micallef et al., "Use of a Special Inhaler Attachment in Asthmatic Children", *Thorax*, vol. 35, pp. 620–623, (1980).

Newman et al., "Deposition of Pressurised Aerosols in the Human Respiratory Tract", *Thorax*, vol. 36, pp. 52–55, (1981).

Poppius, "Inhalation of Terbutaline Spray Through an Extended Mouthpiece", *Respiration*, vol. 40, pp. 278–283, (1980).

Orehek et al., "Patient Error in Use of Bronchodilator Metered Aerosols", *British Medical Journal*, vol. 10, p. 76, (1976).

Graff et al., "Use of Pressurised Aerosols by Asthmatic Patients", *British Medical Journal*, vol. 10, pp. 76–77, (1976).

Bloomfield et al., "A Tube Spacer to Improve Inhalation of Drugs from Pressurised Aerosols", *British Medical Journal*, vol. 10, p. 77, (1976).

Newman et al., "Deposition of Pressurised Aerosols in the Human Respiratory Tract", *Thorax*, vol. 36, No. 1, p. 52, (1981).

Woodcock, "Training Aid for Pressurized Inhalers", *Br. J. Dis. Chest*, vol. 74, pp. 395–397, (1980).

Lindgren et al., "Improved Aerosol Therapy of Asthma: Effect of Actuator Tube Size on Drug Availability", *Eur. J. Respir. Dis.*, vol. 61, pp. 56–61, (1980).

Greico, "In Vivo Comparison of Triamcinolone and Beclomethasone Inhalation Delivery Systems", Annals of Allergy, vol. 45, pp. 231–234, (1980).

Bartlett–Edwards Incentive Spirometer, McGraw Respiratory Therapy, R71-166.

DRUG DELIVERY METHOD AND INHALATION DEVICE THEREFOR

CROSS-REFERENCE TO RELATED APPLICATIONS

This application is a continuation-in-part of copending U.S. patent application Ser. No. 285,992, filed July 23, 1981 and now abandoned, which is in turn a continuation of copending U.S. patent application Ser. No. 280,631, filed June 6, 1981 and now abandoned, which is in turn a continuation of U.S. patent application Ser. No. 142,697, filed Apr. 22, 1980, now abandoned.

BACKGROUND OF THE INVENTION

The invention relates to inhalation apparatus and methods suitable for administering oronasal medication. Further, the apparatus and methods are adapted to permit incentive spirometry with use of the inhalation apparatus.

Oronasal delivery of drugs has been known for some time and gained acceptance for various types of drugs. A metered dose of bronchodilators and steroids from a pressurized aerosol cannistor delivered through the mouth to deliver medicines into the air passageways for delivery to the lungs has become an important method for drug delivery. Despite the potential uses of this type of drug delivery system, patients generally have not made optimum use of the drug delivery devices of this type. Gayrard et al, "Mauvaise utilisation des aerosol-doseurs par les asthmatiques", *Respiration*, Vol. 40, pp. 47-52 (1980), reported that of physician-trained patients in a particular study, approximately half (48%) did not properly use their aerosol devices a month after having received instructions from their physician, while only slightly more than a quarter of those studied (28%) followed the manufacturer's recommendations. Heimer et al, "The Effect of Sequential Inhalations of Metaproterenol Aerosol in Asthma", *J. Alleger. Clin. Immunol.*, Vol. 66, pp. 75-77 (1980), compared $FEV_{1.0}$ in asthmatics after both a single dose and then three sequential doses of 5-[1-hydroxy-2-[(1-methylethyl)amino]ethyl]benzene diol aerosol at intervals of ten minutes. The $FEV_{1.0}$ was greater with the sequential administration, favoring the possibility that airways which were dilated by the initial dose of the brochodilator aerosol permitted the entry of greater aerosol in subsequent administrations. Riley et al, "Enhanced Responses to Aerosolized Bronchodilator Therapy in Asthma Using Respiratory Maneuvers", *Chest*, Vol. 76, pp. 501-507 (1979), studied the administration of 800 ug isoproterenol at 20 or 80% VC versus the administration of 4 doses of 200 ug every twenty (20) minutes to asthmatics. These studies confirmed the findings of Heimer et al, supra, that better bronchodilatation was achieved with sequential administration, and additionally reported that delivery at 80% VC produced more effective bronchodilatation than delivery at 20% VC. Riley et al related the latter finding to the facilitation of aerosol penetration by the greater mechanical opening of the airways at the high lung volume. Newman et al, "Simple Instruction for Using Pressurized Aerosol Bronchodilators", *J. Roy. Soc. Med.*, Vol. 73, pp. 776-779 (1980), found that maximal bronchodilatation as judged by an increase in $FEV_{1.0}$ was achieved when metered terbutaline aerosol 500 ug was employed with a slow, deep inhalation, 25 L/minute, followed by a 10 second breathholding. The lung volume at which the aerosol was inhaled had no effect on the degree of bronchodilatation. Rapid inhalation at 80 L/minute of terbutaline aerosol followed by 4 or 10 second breathholding was less effective than the slow inhalation delivery procedure.

The mass median aerodynamic diameter of commercial metered aerosol preparations is variable and depends upon the method of analysis. Hiller et al, "Simple Instruction for Using Pressurized Aerosol Bronchodilators", *Am. Rev. Resp. Dis.*, Vol. 118, pp. 311-317 (1978), found that nine metered aerosols had a mass median aerodynamic diameter ranging from 2.8 to 4.3 um and a geometric standard deviation ranging from 1.5 to 2.1. Count median diameter was measured with "Spart", a single particle aerodynamic relaxation time analyzer, and the mass median aerodynamic diameter calculated. However, small errors in the estimation of the geometric standard deviation produce major changes in the calculation of the mass median aerodynamic diameter. Kim et al, "Aerodynamic Size Distribution of Metered-dose Aerosols in Low and High Humidity Conditions", *Am. Rev. Resp. Eis.*, Abstract (in press), (1981), reported on measured mass median aerodynamic diameter of metered aerosols by sampling from a large reservoir container through a six-stage Anderson cascade impactor whose plates were coated with petroleum jelly to eliminate the bounce off of particles. Size distributions were approximately log normal and had a mass median aerodynamic diameter ranging from 3.3 to 5.5 um with a geometric standard deviation of 2.0 to 2.2. These diameters were 30 to 60% larger than reported by Hiller et al, supra, but this discrepancy can be reconciled by increasing the geometric standard deviation of these authors by 5 to 10%. For practical purposes, one can take 4 um mass median aerodynamic diameter as an average estimate of particle size delivered by metered aerosol containers.

Metered aerosols are delivered with such a high velocity that a significant fraction is lost to impaction on the tongue and oropharynx before ever reaching the airways. Absorption of adrenergic agonists through the oropharyngeal mucosa can bring about unwanted cardiac effects; deposition of insoluble corticosteroids in the mouth can promote oropharyngeal candidiasis. Impaction of suspension aerosols, e.g., Duo-medihaler, Medihaler-iso, Medihaler-epi, Alupent, in the oropharynx has generally been found to be less than liquid types, e.g., Bronkometer, Mistometer, Berotec. This has been measured with in vivo chemical or analysis of radioisotopically labelled compounds by rinsing the mouth and recovering the drug and with in vitro models through physical methods such as weighing or collection by impingement [Paterson et al, "Method of Using Pressurized Aerosols", *Brit. Med. J.*, Vol. 1, pp 76-77 (1976); Bell et al, "Variation in Delivery of Isoprenaline From Various Pressurized Inhalers", *J. Pharm. Pharmac.* 25, Supp. 32, pp 36P (1973); Laros et al, "Absorption, Distribution and Excretion of the Tritium-labelled $B_2$ Stimulator Fenoterol Hydrobromide Following Aerosol Administration Instillation Into the Bronchial Tree", *Repiration*, Vol. 34, pp. 131-140 (1977); Kim et al, "Delivery Efficiency of Metered-dose Aerosols by Usual Administration and Through a Reservoir Bag", *Am. Rev. Resp. Dis.*, Abstract (in press) (1981)]. Values for loss of aerosol under these circumstance range from 43 to 57% for suspension aerosols and 53 to 90% for liquid aerosols [Paterson et al, supra;

Bell et al, supra; Laros et al, supra]. As reported in "Delivery Efficiency of Metered-dose Aerosols by Usual Administration and Through a Reservoir Bag", we have fabricated a glass model of the adult oropharynx and delivered aerosol from several metered aerosols to its opening while a continuous flow of either 10 or 30 L/minute of dry and humid (90% R.H.) air was passed through it. Aerosol particles passing through the model were collected on a filter at its outlet and weighted with a microbalance. Deposition of suspension aerosols onto the oropharyngeal model using dry air flowing at 30 L/minute ranged from 44 to 54% of administered dose and for liquid aerosols 62 to 69%. These values increased 5 to 15% when the flow rate was decreased from 30 to 10 L/minute at the same humidity or when air with 90% R.H. was employed.

Auxilliary delivery devices are discussed by Lindgren et al, Lindgren et al, "Improved aerosol therapy of asthma: effect of actuator tube size on drug availability", *Eur. J. Respir. Dis.*, Vol. 61, pp. 56–61 (1980), who compared metered terbutaline aerosol alone and in combination with two differently shaped tubes: (a) a straight glass tube (ST) of 100 mm length with an internal diamter of 32 mm (80 ml volume) and a pear-shaped glass tube (PT) of 250 mm length with maximal internal diameter of 130 mm (1000 ml volume). Lindgren et al measured $FEV_{1.0}$ in asthmatics after sequential inhalations of terbutaline at 25 minute intervals. All methods of administration produced an increase in $FEV_{1.0}$ but greater and more prolonged duration of action was observed with the PT. The Lindgren et al disclosure is representative of auxiliary delivery devices that have been introduced in conjunction with metered aerosols to obviate the incorrect usage of delivery systems device common to the prior art and to minimize impaction loss onto the oropharyngeal mucosa. The spacer tube also produced a more effective bronchodilation than metered aerosol alone. In these types of auxilliary delivery devices, the aerosols impact on the walls of the tube rather than on the oropharynx. In another patient study reported by Bloomfield et al, "A Tube Spacer to Improve Inhalation of Drugs From Pressurised Aerosols", *Brit. Med. J.*, Vol. 2, p. 1479 (1979), the spacer tube did not produce a greater increase of $FEV_{1.0}$ compared to metered aerosol when a correct usage of both of the devices was employed.

Apparatus for administering drugs to pulmonary tissue are known in the prior art. Conventional apparatus for administering such drugs are shown, for instance, in U.S. Pat. No. 4,174,712 and other references known to those skilled in the art. These apparatuses have in common a pressurized inhaler bottle containing an aerosol propellant and a medication to be applied to the pulmonary tissue. A nebulizer is associated with the pressurized inhaler bottle whereby the actuation of the combination nebulizer-pressurized inhaler bottle introduces a predetermined dosage of medication to the oronasal cavity area of a patient.

Difficulties with administering this type of medication have been experienced in using the prior art devices. For instance, it is found that direct spraying of the medicant into the oral cavity leaves a substantial portion of the dosage on the patient's tongue and otherwise not in the pulmonary tissue where the drug is required. This particularly poses a problem for steroidal inhalants which have strict limits on total dosage, and on side effects such as promoting fungile growth on the tongue. Further, some patients have difficulty in effecting the inhalation of the medication. The resulting process of delivering the drugs to the pulmonary tissue results in only a portion of the required dosage reaching the tissue area. This requires repeated dosages to be given to the patient so that sufficient medication reaches the pulmonary tissue. In addition, a portion of the inhaled medication is not absorbed, thus it is lost upon expiration. Repeating the dosage also places an unnecessary amount of propellant contained in the pressurized aerosol mist into the respiratory system than is otherwise desired. The processes and apparatus of the prior art therefore do not provide a uniform distribution of pulmonary medication in the respiratory tracts. A further difficulty resulting from these prior techniques is that the rate of distribution of the pulmonary medication is not constant from patient to patient or dosage to dosage.

Conventional inhalers require a simultaneous actuation of a nebulizer and aerosol container with the act of inhalation. This degree of coordination required for use of these devices makes it difficult to administer pulmonary medication to young children and patients unfamiliar with the technique. Further, it has been found that a long and slow inspiration period promotes an efficient distribution of medication to partially occluded airways. The conventional inhalers are not adapted to a long and slow inspiration period as actuation and inhalation steps are conducted simultaneously, often creating a bolus of concentrated medication in the inhaled air.

The prior art incentive spirometer has as a rule been a complicated mechanism offering some difficulty to patients to operate. Further, spirometer technology has been directed to volumetric measurements of the inspiration of a patient. Efforts to simplify spirometer technology are exemplified in our U.S. Pat. No. 4,327,741, granted May 4, 1982, hereby incorporated by reference. Incentive spirometers for conducting therapeutic and prophylactic respiratory maneuvers are described in this reference. These devices, however, do not provide during use a negative thoracic pressure for inhibiting a rapid inhalation. By inhibiting the rapid inhalation, certain therapeutic benefits are realized in an incentive spirometer not attainable in these prior art devices.

As in the case in the inhalation devices, incentive spirometers are desired which encourage a long and slow inspiration period. During respiratory maneuvers, it is advantageous to provide a visual or audible means for a patient to gauge the breathing progress. Some prior art devices are flow controlled, whereby the flow of air is monitored by the device. These devices, however, encourage a rapid inspiratory rate rather than a long, slow inspiration period. Other apparatus detect the volume of air respiration achieved and are in many instances cumbersome and complicated. Typically, they may comprise a calibrated bellows on a flat surface such as a bedside table and are interfaced to the patient with a long flexible hose. These devices have as a final goal a certain volume inspired. There is no direct feedback to the patient as to his progress during breathing until the final volume is achieved.

Furthermore, most of the prior art devices are not capable of providing a dosage of medication while conducting therapeutic maneuvers. The combination of an incentive spirometer with a medicinal inhaler is most promising in treating postoperative atelectasis and for clearing the small airways of the lungs.

SUMMARY OF THE INVENTION

In accordance with a first aspect of the invention, there is provided a method of administering a drug through an oronasal passage for absorption on the mucous tissue of a patient which comprises (a) introducing an aerosol of said drug into an expanded bag and means for communicating said drug with said oronasal passage of said patient and being otherwise substantially impervious to the passage of air; and (b) collapsing said expanded bag while said means for communicating with said oronasal passageway is in position to deliver said drug into the oronasal passage of said patient.

In a preferred embodiment, said collapsing of said expanded bag takes place through a breath intake by said patient, causing such collapse and the administration of the aerosol through said oronasal passage at the rate of the breath intake of said patient. Preferably the patient is given a signal when the maximum desired rate of inhalation is reached. As the signal, any means that will indicate a maximum desirable limit may be used, and preferably, this is a reed whistle which is activated by air flowing at a rate in excess of the maximum desired rate for delivery of said drug. In a preferred embodiment, said oronasal passage is the mouth, and the drug is delivered for absorption on the tracheobronchial tree. The drug is preferably a pulmonary medicine, such as bronchodilator, which may be 5-[1-hydroxy-2-[(1-methylethyl)amino]ethyl]-benzene diol or 4-hydroxy-3-hydroxymethyl-alpha-[(tert-butylamino)methyl]benzyl alcohol. As used herein, 5-[1-hydroxy-2-[(1-methylethyl)amino]ethyl]-benzene diol is preferably in the form of its sulfate, and this drug is therefore to be considered as the sulfate form unless otherwise indicated, it being understood that the compound per se or other pharmaceutically acceptable salt of 5-[1-hydroxy-2-[(1-methylethyl)amino]ethyl]-benzene diol may be used. In a further aspect, said oronasal passage is the nose, and the amount of drug which enters the system of the patient other than through the nasal mucous membranes is minimized by said patient and maximum contact with the nasal mucous tissue is enhanced, further comprising the step, after collapsing said expanded bag, of maintaining said means for communicating with said oronasal passage in contact with the nose and then reexpanding the air bag, whereby the drug passes over the mucous tissues of the nasal passage a second time and the amount of drug which goes beyond the nasal passage for communication with the bronchial or gastrointestinal routes is minimized. As said drug may be mentioned a nasal decongestant, such as 2-(4-tert-butyl-2,6-dimethyl-3-hydroxybenzyl)-2-imidazoline (oxymetazoline, Afrin) and 1-(m-hydroxyphenyl)-2-methylaminoethanol hydrochloride (phenylephrine hydrochloride, Neo-Synephrine hydrochloride) or a systemically active drug, such as scopolamine disclosed in Keith, U.S. application Ser. No. 283,447 filed July 15, 1981.

While treatments via metered dose inhaler effect bronchodilation in patients with airways obstruction, 5-[1-hydroxy-2-[(1-methylethyl)amino]ethyl]-benzene diol delivered by the invention produced greater bronchodilation compared to 5-[1-hydroxy-2-[(1-methylethyl)amino]ethyl]-benzene diol or 4-hydroxy-3-hydroxymethyl-alpha-[(tert-butylamino)methyl]benzyl alcohol delivered by the conventional metered dose inhaler. The increase in $SG_{aw}$ with 5-[1-hydroxy-2-[(1-methylethyl)amino]ethyl]-benzene diol in accordance with the invention over the other treatments was considerable at all times and unlike the conventional metered dose inhaler was still well maintained two hours after its administration. One puff of 5-[1-hydroxy-2-[(1-methylethyl)amino]ethyl]-benzene diol or other bronchodilator administered every two hours with the invention may be a more efficacious means of achieving bronchodilation during symptomatic bronchospasm than the advocated usual dose of two puffs every 4 to 6 hours via the conventional metered dose inhaler.

In a second aspect of the invention, there is provided a drug delivery device for administering a drug contained in an aerosol to an oronasal passage which comprises (a) a piece having one end communicating with said oronasal passage and connected by a bidirectional channel (sometimes hereinafter referred to as channel) through said piece to the opposite end thereof to an airbag opening, said piece having a drug introduction opening for the introduction of a spray containing a drug, said drug introduction opening disposed such that said drug is introduced directly into said air bag through said piece and said airbag opening, in a direction away from said one end;

(b) a collapsible airbag of fixed maximum dimensions which is impervious to passage of air except for communication with said airbag opening; and which in a preferred embodiment also includes (c) signal means in said bidirectional channel to indicate when the rate of passage of said drug exceeds a desirable limit, whereby the patient taking said drug is reminded to decrease the rate of collapse of said airbag, thereby maximizing drug utilization;

said drug delivery device admitting a drug-containing aerosol through said drug introduction opening while said collapsible airbag is at least partially expanded, said drug being introduced into said oronasal passage with the contraction of said collapsible airbag. The signal means provided may be a whistle activated by passage of air from said airbag into said bidirectional channel at a rate in excess of the desirable limit for effective drug utilization, particularly a reed whistle device. The piece is a tube for communication with the mouth, whereby said drug is delivered to the tracheobronchial tree. The collapsible bag advantageously has a first apertured end cap having said airbag opening and a second end cap facing said first apertured end cap, the two end caps being connected by a collapsible material. The collapsible material is advantageously attached to the two end caps so that as said airbag collapses, the facing end caps rotate in relation to each other. In a further embodiment, the piece is a mask shaped for communication with the nose, whereby said drug is delivered to the nasal mucous membranes. The signal means being a preferred embodiment, the invention thus more broadly is directed to a drug delivery device for administering a drug contained in an aerosol to an oronasal passage which comprises a piece having one end communicating with said oronasal passage and connected by a bidirectional channel through the opposite end of said piece to an airbag opening, said piece having a drug introduction opening for the introduction of a spray containing a drug, said drug introduction opening disposed such that said drug is introduced directly into said airbag through said piece and said airbag opening in a direction away from said one end; and a collapsible airbag of fixed maximum dimensions which is impervious to passage of air except for communication with said airbag opening, said drug delivery device admitting a drug-containing aerosol through said drug introduction opening while said collapsible airbag is at least partially expanded, said drug being introduced into said oronasal passage with the contraction of said collapsible airbag.

An airbag (sometimes hereinafter also termed an inflatable envelope), is provided for receiving a measured quantity of aerosolized drug (also sometimes referred to herein as medicament). The airbag or envelope has interior surfaces which confine the received drug or medicament and an opening for delivering the drug or medicament to a patient. A piece is provided in communication with the opening for conducting to the patient's mouth or nose the drug in the airbag which becomes mixed with a predetermined amount of air. The patient evacuates the airbag by applying a negative pressure to the mouthpiece. Means are provided on the interior surface of the envelope to maintain them apart, thereby preventing collapse of the envelope. In a preferred embodiment of the apparatus according to the invention, medicament is discharged into the envelope through a small nebulizer connected to a pressurized inhaler bottle. When a predetermined quantity of aerosol and medicament is discharged from the bottle, the discharged stream is directed into the envelope. The envelope is connected to a mouthpiece serially connected with the nebulizer. The resulting structure permits the medicament to enter the envelope in a first direction, and upon the application of a negative pressure to the mouthpiece by the patient, the contents of the envelope are delivered in a second direction which is opposite to the inflating direction and thus to the patient's pulmonary tissue. By first filling the envelope with the aerosolized medicament, and then withdrawing the contents of the envelope into the patient's respiratory system, controlled inhalation of the medicament results, improving the rate and distribution of the medication in the respiratory tracts.

In accordance with a third aspect of the invention, there is provided a kit suitable for assembly into said drug delivery device which comprises a piece having one end to communicate with said ornasal passage and connected by a bidirectional channel through said piece to the opposite end thereof to an airbag opening, said piece having a drug introduction opening for the introduction of a spray containing a drug, said drug introduction opening disposed such that said drug is introduced directly into an airbag through said piece and an airbag opening in a direction away from said one end; and a collapsible airbag of fixed maximum dimensions which is impervious to passage of air except for said airbag opening adapted for snug fitting with said bidirectional channel. In a preferred embodiment, the collapsible bag has a first apertured end cap having said airbag opening and a second rigid end cap facing said first apertured end cap, the two end caps being connected by a collapsible material.

In a fourth aspect of the invention, there is provided an incentive spirometer which comprises a piece having one end communicating with a patient's mouth and connected by a bidirectional channel through said piece to the opposite end thereof to an airbag opening; a collapsible airbag of fixed maximum dimensions which is substantially impervious to passage of air except for communication with said airbag opening; the signal means in said bidirectional channel to indicate when the rate of passage of air reaches a desirable limit, whereby the patient taking a breath is reminded to decrease his breathing to the level below which said signal means is operated. The incentive spirometer preferably has as the signal means a whistle which may be a reed activated by passage of air from said airbag into said bidirectional channel at a rate in excess of the desirable limit for effective drug utilization. Preferably said collapsible bag has a first apertured end cap having said airbag opening and a second end cap facing said first apertured end cap, the two end caps being connected by a collapsible material, and said collapsible material is attached to the two end caps so that as said airbag collapses, the facing end caps rotate in relation to each other.

In accordance with this fourth aspect of the invention, means for simultaneously monitoring flow rate and volume inspired during a respiratory maneuver are provided, as are means to provide a hand-held incentive spirometer. The incentive spirometer facilitates holding a sustained maximal inspiration without glottal closure and provides an incentive spirometer which is capable of administering pulmonary medication in conjunction with respiratory maneuvers. Visual and tactile observation of respiratory maneuvers is facilitated, and there is provided an incentive spirometer which facilitates a negative thoracic pressure during a respiratory maneuver.

Apparatus in accordance with the second aspect of the invention may also be used as an incentive spirometer. Specifically, by inspiring through the mouthpiece, it is possible to sequentially deflate and inflate the envelope. The means for maintaining the interior surface of the envelope apart will prevent occlusion of the envelope which interferes with a total evacuation of the envelope. With this structure, a consistent volume of air may be inspired. The envelope is preferably detachably connected to a mouthpiece or nebulizer to permit different-sized envelopes to be used to correspond accurately to the volume capacity of a patient. Additional embodiments of an incentive spirometer according to the invention may provide an auditory signaling device for warning when a too rapid flow rate has been attained. The signaling device, e.g., a reed whistle, will therefore permit the patient to control the rate of inhalation. A further embodiment for controlling inhalation with a spirometer according to the invention provides for a series resistor means in the mouthpiece of a spirometer to produce a negative intrathoracic pressure which inhibits a rapid inhalation. Therefore, a controlled slow inhalation is made possible. A further embodiment of the apparatus is that the patient can exhale back into the plastic envelope and re-inspire over several breaths to aid in depositing the aerosolized medicant which has not settled in the lung from previous breaths. This increases the effective dose of the medicament.

DETAILED DESCRIPTION OF THE INVENTION

Figure 1:
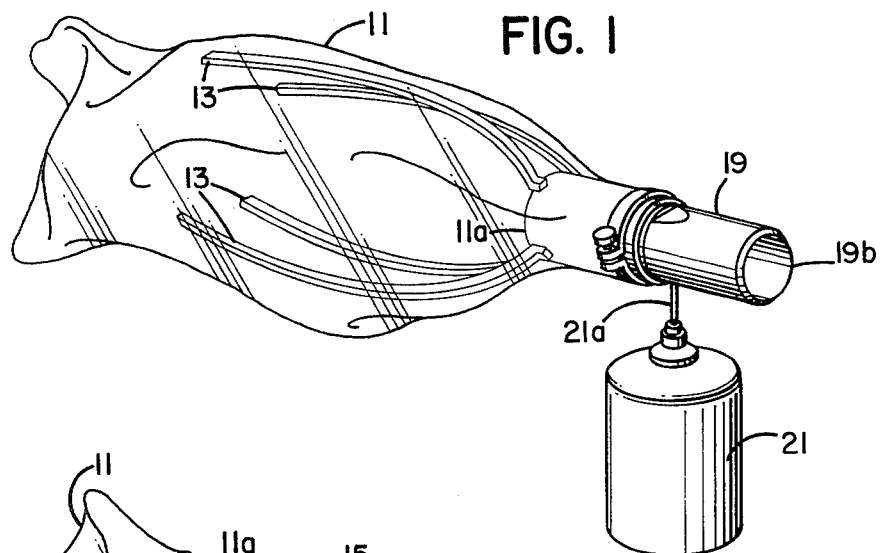
FIG. 1 is an overall view of an inhaler device in accordance with a preferred embodiment.

5-[1-Hydroxy-2-[(1-methylethyl)amino]ethyl]-1,3-benzene diol in the form of its sulfate is a widely used brochodilator (metaproterenol, Alupent, Metaprel, Alotec, Novasmasol). Another drug in this same general category is 4-hydroxy-3-hydroxymethyl-alpha-[(tert-butylamino)methyl]benzyl alcohol (Aerolin, Broncovaleas, Sultanol, Ventlin, Ventolin, Proventil). In accordance with the additional modes of application, the manufacturer of 5-[1-hydroxy-2-[(1-methylethyl)amino]ethyl]-benzene diol recommends a metered dose inhaler having 225 mg micronized powder in an inert propellant, which has approximately 300 doses. The drug is contained in a 15 ml inhaler which fits into a mouthpiece for administration of the drug. Two to three "puffs" of inhalant is a usual dosage, repetitive dosing to be taken not more than about every three to four hours, with a total dosage per day maximum of about 12 such "puffs" of inhalant. According to *Facts and Comparisons*, p. 586 (1980), deaths have been reported following excessive use of inhalation preparations, it being stated that the exact cause is unknown, with cardiac arrest having been noted in several instances. It is also stated that in patients with status asthmaticus and abnormal blood gas tensions, improvement in vital capacity and in blood gas tensions may not accompany an apparent relief in bronchospasm. Also reported for 5-[1-hydroxy-2-[(1-methylethyl)amino]ethyl]-benzene diol is the observation that in occassional patients, a severe paradoxical airway resistance takes place with repeated, excessive use of inhalation preparations. It is reported for 4-hydroxy-3-hydroxymethyl-alpha-[(tert-butylamino)methyl]benzyl alcohol [*Physician's Desk Reference*, p. 662 (1981)] that excessive use of adrenergic aerosols is potentially dangerous. Fatalities have been reported following excessive use of Alupent metered dose inhaler, brand of metaproterenol sulfate, as with other sympathomimetic inhalation preparations. It is particularly noted in this PDR reference that "[e]xtreme care must be exercised with respect to the administration of additional sympathomimetic agents. A sufficient interval of time should elapse prior to administration of another sympathomimetic agent. *** [I]t should be used with great caution in patients with hypertension, coronary artery disease, congestive heart failure, hyperthyroidism and diabetes, or when there is sensitivity to sympathomimetic amines." In addition, it should be particularly appreciated that with the traditional "puff" of aerosol such as is commonly used with drugs such as 5-[1-hydroxy-2-[(1-methylethyl)amino]ethyl]-benzene diol or 4-hydroxy-3-hydroxymethyl-alpha-[tert-butylamino)methyl]benzyl alcohol the quick administration of the drug into the mouth is not accompanied by a sudden uptake of air into the patient's lungs that would take advantage of the aerosol's action to substantially deliver the drug into the patient's tracheobronchial tree, much of the drug instead not going into this desired area, but being delivered into the gastrointestinal tract, the very antithesis of the administration of an aerosol drug such as 5-[1-hydroxy-2-[(1-methylethyl)amino]ethyl]-benzene diol that is designed for delivery into the tracheobronchial tree. This problem is implicitly recognized in the Proventil (Schering) "Patient's Instructions for Use" for the aeresol 4-hydroxy-3-hydroxymethyl-alpha-[(tert-butylamino)methyl]benzyl alcohol preparation, which includes the following instructions:

2. Breathe out fully, expelling as much air from your lungs as possible. ***

3. While breathing in deeply, fully depress the top of the metal cannister ****

4. Hold your breath as long as possible. ***

In other words, the traditional "puff" of aerosol medication is recognized as being not completely satisfactory by the experts themselves, who attempt to have as much of the drug reach the tracheobronchial tree as possible by having the patient breath in very deeply at the very time he administers the puff of aerosol, and then have the patient hold his breath for as long as possible. It is not surprising that this is a difficult procedure to follow, in accord with the published findings of Gayrard et al, supra, that only little more than a quarter of the patients observed in his study even followed this type of instruction.

Another drug that has been administered through inhalation is 9-chloro-11beta,17,21-trihydroxy-16beta-methyl-pregna-1,4-diene-3-,20-dione 17,21-dipropionate, beclomethasone dipropionate [Beclovent (Glaxo)], which is dispensed from a similar inhaler as a metered-dose "puff" which contains a microcrystalline suspension of 9-chloro-11beta,17,21-trihydroxy-16beta-methyl-pregna-1,4-diene-3-,20-dione 17,21-dipropionate trichloromonofluoromethane clathrate in a mixture of trichloromonofluoromethane and dichlorodifluoromethane propellants in oleic acid. Each actuation delivers a "puff" of 42 mcg of 9-chloro-11beta,17,21-trihydroxy-16beta-methyl-pregna-1,4-diene-3-,20-dione 17,21-dipropionate, providing about 200 oral "puffs".

In accordance with a further aspect of the invention there is provided as the oronasal route the selection of the nasal administration of drugs. This route of administration is indicated where a localized administration of the drug to contact the nasal passages is indicated for relief in that area with drugs such as phenylepinephrine hydrochloride (Neo-Synephrine, Winthrop) or oxymetazoline hydrochloride (Afrin, Schering), as well as situations where systemic uptake of a drug through the nasal mucous tissues is indicated to avoid the problems often associated with oral administration of drugs. For example, whereas scopolamine is an effective motion sickness drug the pass through the liver makes this mode of administration unsatisfactory, passage through the nasal mucous membrane avoiding a first pass through the liver associated with oral administration of the drug, and also providing a relatively rapid delivery of the drug superior in that regard to transdermal medication of the drug which has a delayed action versus nasal administration. See copending and commonly owned application Ser. No. 283,447, filed July 15, 1981, "Motion Sickness Spray Composition and Method" of Alec D. Keith, incorporated herein by reference. The delivery of nasal decongestants is particularly indicated in accordance with the invention, with two particular advantages over the prior art inhalants. In the prior art inhalants, the drug is administered by giving a quick puff into the nose, with the result being that most of the drug hits the nasal passage at the front of the nose, only a minor amount of the drug hitting the back portion of the nasal passages. With the regular "breathing" in of the drug in accordance with the invention, it is seen that a more even passage of the drug throughout the nasal membrane area occurs. In addition, the drug that is traditionally "shot" into the nose may pass into the body, as the patient breathes in further after administration of the quick puff. In accordance with the invention, after administration of the drug, and before further breathing by the patient, the apparatus of the invention is operated to *remove* the identical volume of air that had been administered, i.e., evacuating the same amount of air from the nasal passages as had been administered, thereby providing a second pass of the drug through the nasal passage as the drug is withdrawn and to eliminate *all* of the unabsorbed drug, so that essentially none of the drug enters the body of the patient except through the sought entry through the nasal mucous tissue.

FIG. 1 is a perspective view of an inhaler device in accordance with an embodiment of the invention. For convenience, it is shown in an inverted position and it should be understood that for most medicaments it would be used with bottle 21 extending downwardly. Plastic envelope 11 is provided having a plurality of interior surfaces which confine the medicament to be inhaled by a patient. Plastic envelope 11 has, within its interior, a means for maintaining the surfaces apart which preferably comprises a plurality of resilient plastic stays 13 extending the length of the interior surfaces of plastic envelope 11. The four plastic stays 13 shown in FIG. 1 maintain the interior surfaces apart and after collapse of the bag, as a result of a negative pressure being applied to outlet 11a thereof, the stays will force the interior surfaces of plastic envelope 11 apart. When used as a spirometer, the stays prevent occlusion by virtue of air becoming trapped in the plastic envelope due to the interior surfaces contacting each other.

The inhaler device is used in connection with inhaler bottle 21 which introduces a micronized medicament into envelope 11. Once the envelope has received a charge of medicament from inhaler bottle 21, the patient applies a negative pressure through his lips to free end 19b of mouth piece 19. The contents of envelope 11 are thus drawn into the oral cavity of the patient.

Figure 2:
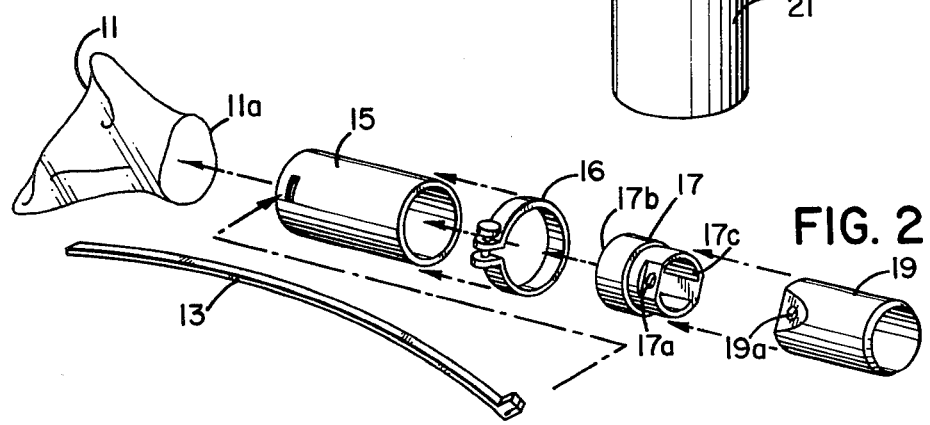
FIG. 2 is an exploded view of an inhaler apparatus as in a preferred embodiment of the invention.
Figure 3:
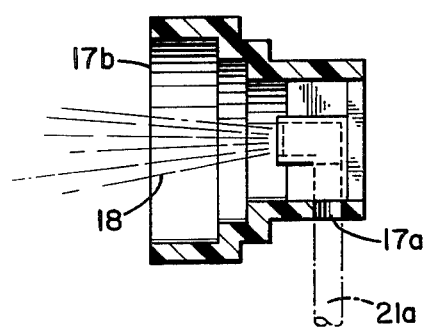
FIG. 3 is a longitudinal cross sectional view of a nebulizer suitable for use in the preferred embodiment of FIG. 1.

FIG. 2 shows an exploded view of the device of FIG. 1. Plastic ring 15 (or sometimes hereinafter referred to as sleeve 15) is provided for mounting four plastic stays 13 and plastic envelope 11. The ring holds open an aperture at one end of the envelope whereby the medicant may be received and later discharged therethrough. Nebulizer 17 is shown in association with plastic ring 15, in FIG. 3; the nebulizer communicates in a sealing fashion with plastic ring 15. Inhaler bottle 21 and nebulizer 17 may be of a type available from Breon Company sold as Bronchometer (TM) No. 1740 as part No. 7-1040-01. Nebulizer 17 may have outlet 17b which has an outside diameter of a size to define an interference fit with the interior diameter of plastic ring 15. Ring 15 is attached to plastic envelope 11 either by applying tape, or by small clamp 16 which may be easily removed by the patient using the device. Nebulizer 17 is utilized by those skilled in the art to provide aerosol mist 18 in response to the ejection through opening 17a of a stream of aerosol propellent containing the desired medicament. Nebulizer 17 interfaces with pressurized inhaler bottle 21 so that pressure applied to the nebulizer will discharge the micronized medicament through outlet 17b in a vapor stream. Through channel 17c permits the medicament in the envelope to return and pass through to piece 19 (the piece is sometimes hereinafter referred to as a mouthpiece).

Mouthpiece 19 has an inside diameter which fits snugly over with the outside diameter of nebulizer 17. Opening 19a on the mouthpiece aligns with opening 17a of the nebulizer. The stem of an inhaler bottle 21 may therefore protrude through openings 19a and 17a to contact a shoulder located within the nebulizer. By displacing stem 21a longitudinally with respect to the inhaler bottle 21, a predetermined dosage of medicament is released. Nebulizer 17a directs the medicament into plastic envelope 11 which mixes the then micronized medicament with air therein.

To use the device shown in FIG. 1, the patient places the free end of mouthpiece 19b in his mouth. A quantity of medicament is discharged by moving inhaler bottle 21 relative to nebulizer 17. A predetermined dosage of aerosolized medicament is thereafter deposited within plastic envelope 11. When the patient applies a negative pressure to the free end of mouthpiece 19b, the medicament stored within plastic envelope 11 is drawn through opening 17c in the nebulizer towards mouthpiece 19 and into the respiratory system of the patient. Thus, with the device of FIG. 1, it is possible to administer pulmonary medication into a two-step process. A patient, even a small child, can first discharge the aerosol medicament into plastic envelope 11, and thereafter breathe in the medicament to achieve a uniform dosage. By first directing the medicant into envelope 11, the coarser spray from the nebulizer is dispersed in the envelope reducing any impaction on the tongue of micronized medicament which would occur from the coarser spray of the nebulizer when introduced directly to the oral cavity. In addition, the patient can exhale back into the plastic envelope and re-inspire once again over several breaths to aid in depositing the aerosolized medicament which has not settled in previous breaths. This increases the effective dose of the medicament.

Figure 4:
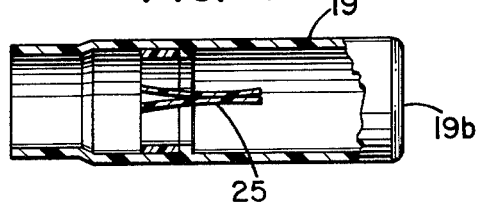
FIG. 4 is a top view, partially in cross section, of a preferred mouthpiece for use in an incentive spirometer.

FIG. 4 illustrates yet another embodiment in accordance with the invention having audio enunciator 25 for indicating when the flow rate through the mouthpiece is too rapid. With the audio enunciator, which may be a simple reed whistle responding to an excessive flow rate, the patient is made aware by yet another means of his breathing performance as it relates to the air flow rate out of the envelope.

Figure 5:
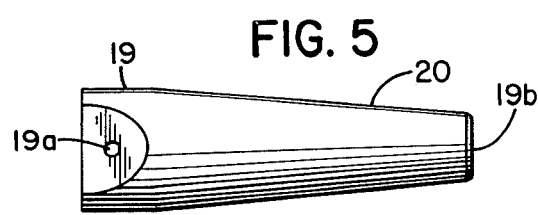
FIG. 5 is a top view of yet another embodiment of an incentive spirometer whereby a reed device is placed in the mouthpiece for indicating the flow rate therethrough.

FIG. 5 is yet another embodiment of a spirometer in accordance with the invention wherein the mouthpiece contains restriction 20 which limits the air flow into and out of the spirometer. By including such a restriction device, the patient's breathing rate may be controlled so that a predetermined flow rate may be established in the incentive spirometer. Those skilled in the art will recognize therapeutic and prophylactic advantages resulting from such control.

Thus, with the device shown in FIG. 1, it is possible to both administer pulmonary medication and conduct respiratory exercises in conjunction with the administration of pulmonary medication. The device provides for a long, slow inspiration period when distributing medication to the occluded airways, as well as providing the long and slow inspiration period during respiratory exercises which are desirable in treating postoperative atelectasis and clearing small passageways of the lungs.

A further variation on the embodiment of FIG. 1 can include a mask connected to the mouthpiece which will facilitate the use of the device with children. The mask will snugly fit over the face of the children and breathing into the envelope facilitated.

Figure 6:
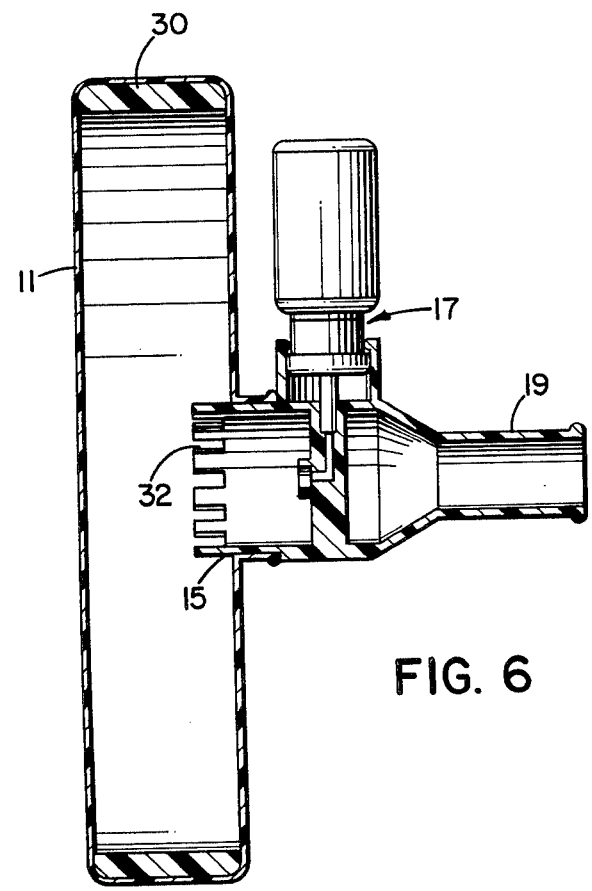
FIG. 6 is a side view, partially in cross section, showing the use of this invention in connection with a relatively stiff foam rubber spring for the air bag.

It is contemplated that air bag 11 may be designed in several different forms as shown in FIGS. 6–11. These figures show nebulizer 17 in an upright position. In FIG. 6, envelope 11 is in the form of a balloon bag which may be dip molded and shaped with an opening to define a stretch fit around tube 15. This tube has slots 32 on its inner end which upon inhalation, prevent closing off of the ends of the breathing tube by the collapsing bag. A relatively stiff foam rubber spring 30 is used to maintain the bag in its radially outwardly stretched position. Upon inhalation the bag can collapse to a limited extent, moving both radially inwardly toward sleeve 15 and axially inwardly toward slots 32.

Nebulizer 17 of this embodiment acts in the same manner as the nebulizer previously described. Similarly, there is open passage way 17c to permit air to return from the air envelope to mouthpiece 19. The nebulizers in FIGS. 7–10 are similar and will not be separately described in detail. However, it should be noted that in all cases the outlet from the medicant supply faces toward the air bag so that the medicant is first deposited into the bag and mixed with air and then, upon subsequent suction inhalation by the patient, the aerosolized mixture then moves upstream toward the mouthpiece.

Figure 7:
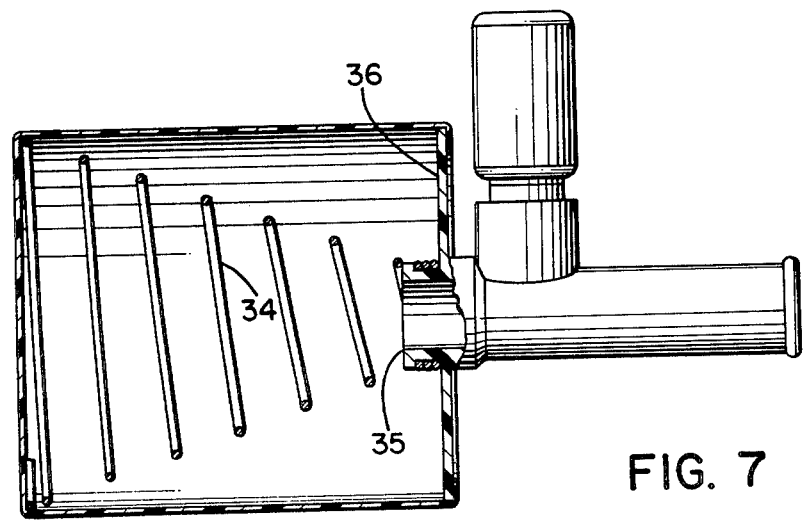
FIG. 7 is a side view, partially in cross section, showing another use of this invention with conical spring stays.

In FIG. 7, bag 11, which may in one embodiment be of condom type material, is held in its extended position by conical spring stay device 34 which, when it is in its collapsed position, will form a substantially flat spiral concentrically about end 35 of the breathing tube and against end wall 36 of the device.

Figure 8:
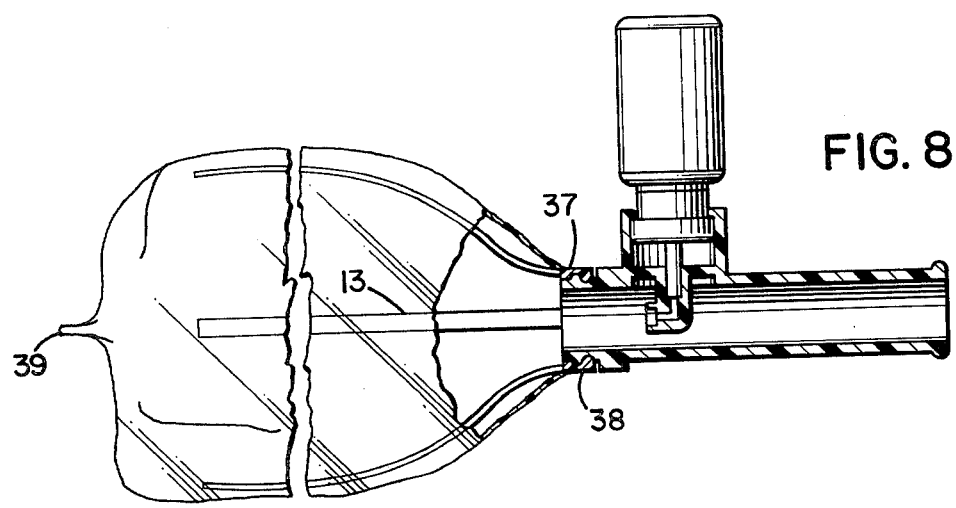
FIG. 8 is a side view similar to FIG. 1, partially in cross section, utilizing plastic spring fingers inside the air bag.

The inhalation device of FIG. 8 is similar to that of FIG. 1 but with a film bag which is held in place by ring 37 which fits over detent ring 38 on the end of the breathing tube. This bag can be fastened with heat-sealed distal end 39 and is kept open by plastic leaf springs 13 in the same manner as in the embodiment of FIG. 1.

Figure 9:
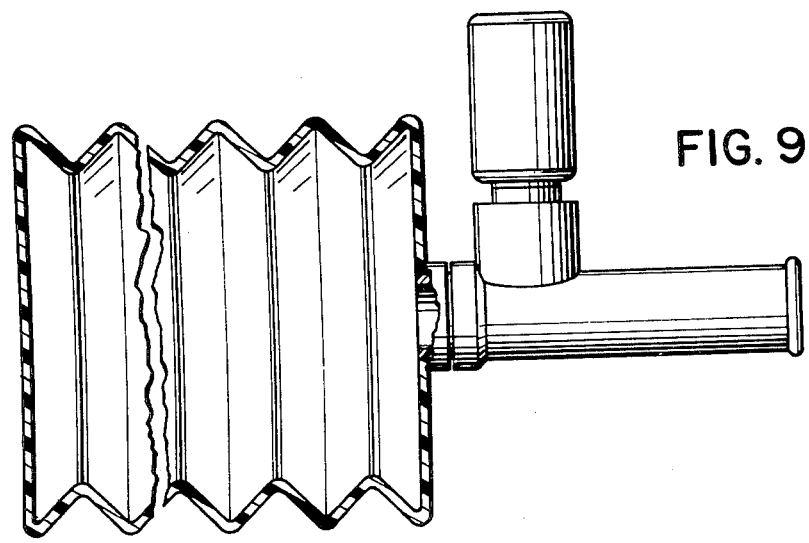
FIG. 9 is a side view, partially in cross section, showing the air bag in the form of a plastic dip-molded bellow.

In the embodiment of FIG. 9 the air bag is formed in the shape of a bellows which can collapse to a substantially flat position when not in use. This bellows can be formed of relatively thin polyethylene material such as 0.005 to 0.010 mil thickness material.

Figure 10:
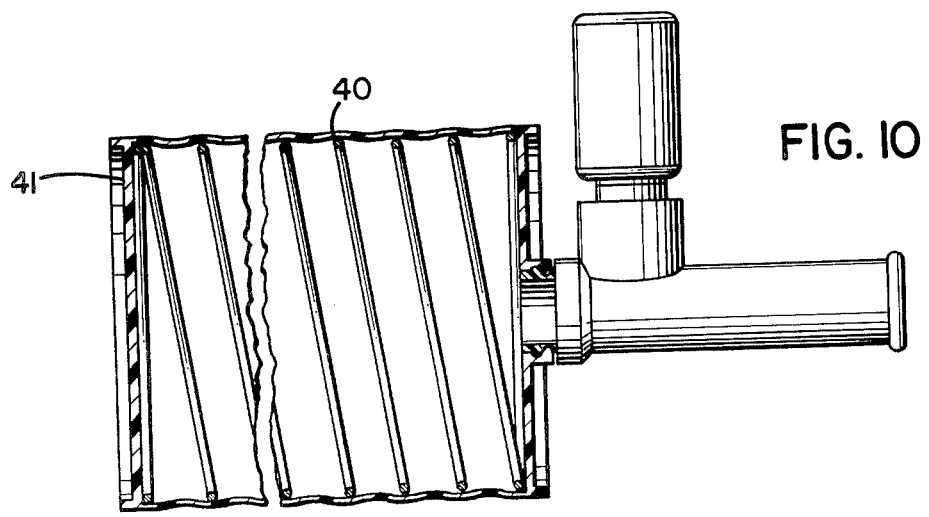
FIG. 10 is a view, partially in cross section, showing the air bag with a compression spring.

The device of FIG. 10 is similar to that of FIG. 9 but with compression spring 40 which is helically wound so as to radially outwardly support the walls of the bag which may be of relatively thin plastic material. The coil can, for example, comprise 6 coils of 0.03 diameter music wire or a plastic material which is comparably resilient and light in weight. In both FIGS. 9 and 10 the bellows can be held to the breathing tube by a detent similar to that of FIG. 8. End cap 41 can be heat sealed to the plastic material used for the side wall. The materials would be selected so that the bag could compress axially due to breathing by a user.

Figure 11:
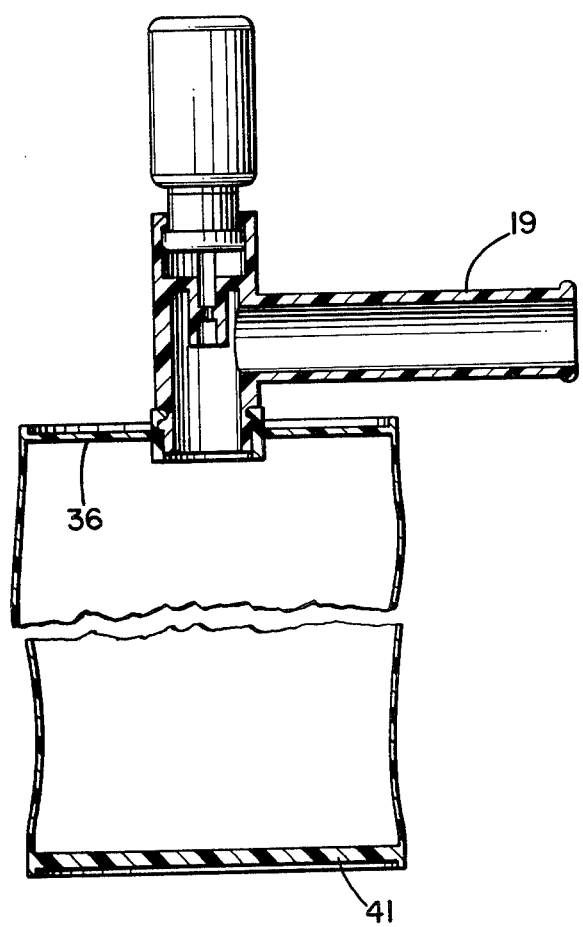
FIG. 11 is a view, partially in cross section of the invention, utilizing a gravity operated air bag.

In FIG. 11, no positive spring pressure is necessary to maintain the bag in its open position because it is vertically arranged so as to be forced open by the effect of gravity with the breathing tube having a 90° bend in it. Thus, as mouthpiece 19 is held in a patient's mouth, the medicament bottle of the nebulizer 17 would normally face upwardly as shown in FIG. 11 while end cap 41 hangs downwardly to hold the air bag open. The end cap is preferably of plastic material and of sufficient weight so as to hold the bag in its open position when no inhaling force is being applied but to permit the bag to partially collapse when the patient draws inwardly on the mouthpiece. The bag would preferably be made of a plastic film material which is heat-sealed both to end cap 41 and to opposite wall 36. Because of the 90° bend in the breathing tube, the medicament bottle is positioned so as to spray its contents directly into the air bag as in the previous discussion, although in this case the path of the discharging medicament is, for a portion of its travel, perpendicular to the air flow path rather than being directly opposite to it as previously discussed. In all cases the operation is the same, to permit mixture of the aerosolized medicament with the air in the bag prior to inspirational breathing by the patient.

Figure 12:
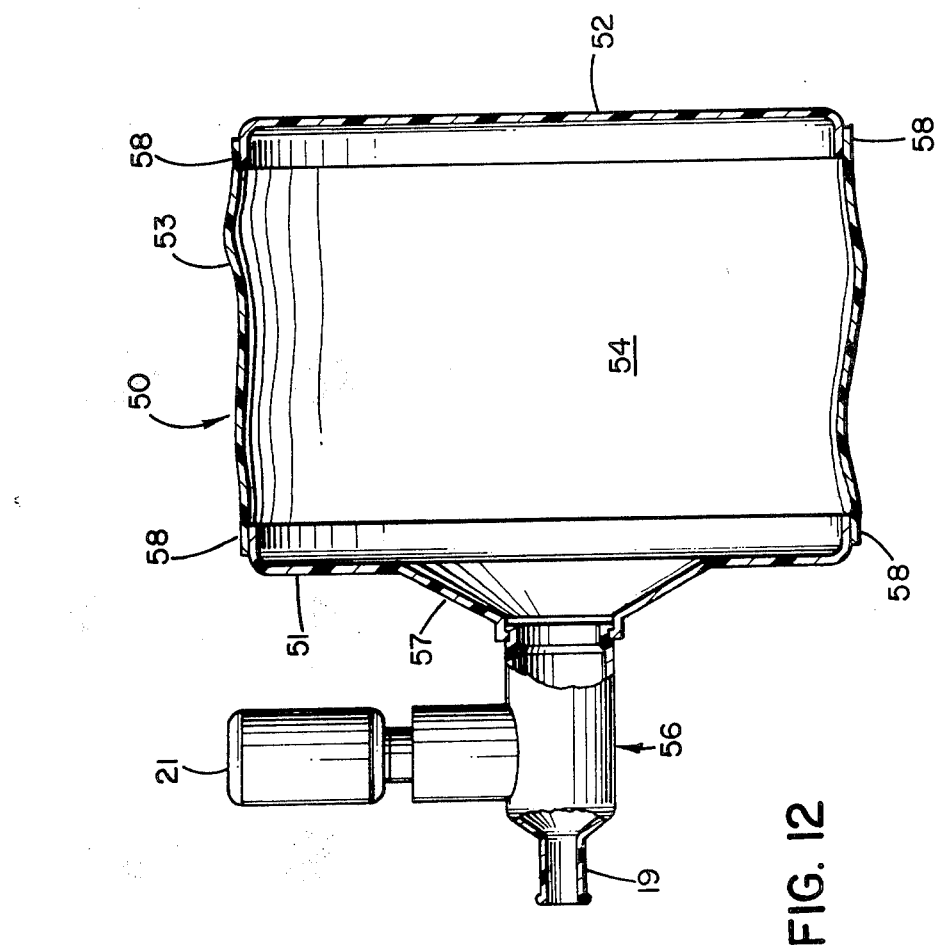
FIG. 12 is a cutaway, partial cross sectional view of another embodiment of the invention as used for oral inhalation.

FIG. 12 employs a basic nebulizer assembly 56 as shown in FIGS. 6–11 with mouthpiece 19 and pressurized inhaler bottle 21. Nebulizer assembly 56 attaches to mounting portion 57 of airbag assembly 50. Airbag assembly 50 is comprised of apertured end cap 51 and end cap 52 connected together by sidewalls 53. Apertured end cap 51, end cap 52, and sidewalls 53 form cavity 54. Apertured end cap 51 and end cap 52 may be made of commercially available plastic material. It is contemplated that walls 53 are made of $2\frac{1}{4}$ mil polyethylene, although they may be composed of any suitably flexible and light material. Side walls 53 would be connected to apertured end cap 51 and end cap 52 by heat sealing around the peripheries 58 thereof. The design of air bag assembly 54 can be of any suitable materials such that it provides a gas impermeable, closed bag that may be attached to nebulizer assembly 56. It is particularly contemplated that the apertured end cap and the end cap may be manufactured in such a manner that it is easily portable and may fit in the pocket of any user. When apertured end cap 51 is detached from nebulizer assembly 56 with a twisting motion, apertured end cap 51 may be rotated in relation to end cap 52 to form a flat assembly with apertured end cap 51 resting on end cap 52 and side walls 53 automatically folded up therebetween. These pieces, working in concert, provide for an easily assembled and easily used, highly effective apparatus. The device of FIG. 12 has a 700 ml collapsible bag in which aerosol is injected. The bidirectional means for communication with the oronasal passage in the mouthpiece is filtered with a reed which vibrates at inspiratory flows greater than 0.3 L/sec to produce a noise. Patients are instructed to keep inhalation silent while breathing. One puff of 5-[1-hydroxy-2-[(1-methylethyl)amino]ethyl]-benzene diol (650 ug) administered via the device of FIG. 12 (with one breath rebreathed) is compared to 1 puff each of 5-[1-hydroxy-2-[(1-methylethyl)amino]-ethyl]-benzene diol (650 ug) and 4-hydroxy-3-hydroxymethyl-alpha-[(tert-butylamino)methyl]benzyl alcohol (100 ug) from usual metered dose inhaler utilizing serial measurements of body plethysmography and spirometry. Respiratory inductive plethysmography measured point of metered dose inhaler actuation, volume of inhalation, inspiratory flow and breathholding pause. Ten patients with chronic airflow limitation due to asthma or chronic bronchitis were given typed instructions on metered dose inhaler usage and trained shortly before the study. 5-[1-hydroxy-2-[(1-methylethyl)amino]ethyl]-benzene diol via the device of FIG. 12 produced significantly greater maximal increase in $SG_{aw}$ 195±52% (SE) compared to 5-[1-hydroxy-2-[(1-methylethyl)amino]ethyl]-benzene diol or 4-hydroxy-3-hydroxymethyl-alpha-[(tert-butylamino)methyl]benzyl alcohol via conventional metered dose inhaler, 101±24% and 86±26%, respectively (p less than 0.003). Bronchodilator response in four patients unable to coordinate actuation of the metered dose inhaler with inspiration was significantly less than in six patients with good metered dose inhaler technique (p less than 0.005). The mean flow rates were 1.02±0.29 L/sec and 0.54±0.16 L/sec during inhalation of SPT and 5-[1-hydroxy-2-[(1-methylethyl)amino]ethyl]-benzene diol, respectively, compared to 0.19±0.02 L/sec and 0.24±0.03 L/sec during the first and second inhalations, respectively, using the device of FIG. 12. This device was well accepted by the patients and promotes more effective bronchodilation than conventional metered dose inhalers. The efficacy of the device of FIG. 12 was compared using one puff of 5-[1-hydroxy-2-[(1-methylethyl)amino]ethyl]-benzene diol to one puff of 5-[1-hydroxy-2-[(1-methylethyl)amino]ethyl]-benzene diol and· 4-hydroxy-3-hydroxymethyl-alpha-[(tert-butylamino)methyl]benzyl alcohol delivered by conventional metered dose inhaler in 10 patients with chronic airways obstruction. All the patients were trained in the use of metered dose inhaler a few days before the study and their technique was nonobtrusively assessed during the trial utilizing respiratory inductive plethysmography. Five male and five female patients with chronic airflow limitation, seven of whom had asthma, and three with chronic bronchitis were studied with the results tabulated below in Table I.

TABLE I
CHARACTERISTICS OF PATIENTS

| | | | | | | | Maximal % Increase In $SG_{aw}$ | | | |
|---|---|---|---|---|---|---|---|---|---|---|
| | | Age | Baseline FEV$_1$ | | $SG_{aw}$ | Clinical | MDI OF THE PRIOR ART | | : | INVENTION (Figure 12) |
| PATIENT | Sex | (Year) | (L) | (% PRED) | (1/sec/cmH$_2$O/1) | Diagnosis | A | B | : | B |
| 1 | M | 43 | 1.42 | 38 | .023 | Asthma | 267 | 200 | : | 300 |
| 2 | M | 76 | 1.65 | 66 | .050 | Asthma | 100 | 225 | : | 160 |
| 3 | F | 76 | 1.99 | 124 | .080 | Asthma | 56 | 71 | : | 125 |
| 4 | N | 50 | .77 | 22 | .023 | Asthma | 33 | 0 | : | 267 |
| 5 | M | 41 | 3.0 | 80 | .033 | Asthma | 192 | 161 | : | 600 |
| 6 | F | 61 | .87 | 36 | .046 | Asthma | 43 | 116 | : | 133 |
| 7 | F | 76 | .90 | 46 | .038 | Asthma | 15 | 31 | : | 103 |
| 8 | F | 77 | .78 | 43 | .037 | Chronic Bronchitis | 50 | 125 | : | 100 |
| 9 | F | 65 | .98 | 51 | .050 | Chronic Bronchitis | 60 | 40 | : | 120 |
| 10 | M | 74 | .88 | 31 | .049 | Chronic Bronchitis | 46 | 38 | : | 37 |

A = 4-hydroxy-3-hydroxymethyl-alpha-[(tert-butylamino)methyl]benzyl
B = 5-[l-hydroxy-2-[(1-methylethyl)amino]ethyl]-benzene diol
MDI = Metered Dose Inhaler The age ranged from 41 to 77 years (mean 64). At the time of the investigation, no patient was suffering from an exacerbation of their illness. Prior to the study, all patients showed an increase in forced expiratory volume in 1 sec (FEV$_1$) of at least 15% and at least 45% increase in specific airway conductance ($SG_{aw}$) after three deep breaths of aerosolized racemic epinephrine or isoetharine delivered by D$_{30}$ generator. The patients were requested to stop their usual metered dose inhaler for at least 9 hours and theophylline for at least 16 hours before each study day. Those taking oral corticosteroids continued on the maintenance dosage.

All subjects underwent pulmonary function testing in the seated position. Measurement of the forced expiratory volume in one second (FEV$_1$) and forced vital capacity were obtained with a dry rolling seal spirometer (Ohio 800, Ohio Medical Products, Houston, Tex.). Airway resistance ($R_{aw}$) and functional residual capacity (FRC) were measured by body plethysmography. Specific airway conductance was calculated by dividing the reciprocal of $R_{aw}$ by the thoracic gas volume at which $R_{aw}$ was measured. Baseline values were recorded and were repeated at 15, 30, 60 and 120 minutes after administration of bronchodilator. The mean and maximum of three measurements of body plethysmography and spirometry, respectively, were used in statistical analysis.

The test involved the device of FIG. 12, with the airbag in expanded form having a 9 cm diameter and a 11.5 cm length. The nozzle of a canister containing aerolized 5-[1-hydroxy-2-[(1-methylethyl)amino]ethyl]-benzene diol was inserted into the piece. 650 ug of aerosolized 5-[1-hydroxy-2-[(1-methylethyl)amino]ethyl]-benzene diol was injected. The patients were instructed to inflate the bag, actuate the aerosol canister, inhale from the bag until it was empty, breathhold while slowly counting to five, exhale back into the bag, and again inhale and breathhold while counting slowly to five. They were requested to inhale slowly in order to prevent the reed from making the sound.

The size distribution of aerosol delivered by metered dose inhaler was measured by using a 6-stage cascade impactor (Anderson Samples Inc., Atlanta, GA). Impaction loss of the metered dose inhaler aerosols on the surface of the oropharynx under the conditions of usual delivery mode was determined by using a glass model of the adult oropharynx which had similar dimensions to a commercial model (Laerdal Medical Corp., Tuckahoe, NY 10707). The metered dose inhaler was connected to the mouth of the glass model and the aerosol was delivered directly into the model while 0.5 L/sec of dry air was continuously passed through the model. Aerosol particles escaping from the pharyngeal end of the model were collected on a filter and weighed.

To estimate the influence of the number of breaths rebreathed in enhancing deposition of aerosol in the airways, a monodisperse aerosol of 4.0 um mass medium aerodynamic diameter was delivered into the device of FIG. 12 and decrease of aerosol concentration was monitored continuously by a light scattering aerosol photometer while a subject rebreathed the aerosol at a rate of 30 breaths/minute. The aerosol was generated by a Sinclair-LaMer type aerosol generator using di-2 (ethyl hexyl) sebacate oil. Size distribution of the aerosol was measured by a Rayco 220 optical counter with a multichannel analyzer.

Drug administration protocol involved a study conducted on a modified randomized single-blind crossover basis. The patient did not know whether 5-[1-hydroxy-2-[(1-methylethyl)amino]ethyl]-benzene diol or 4-hydroxy-3-hydroxymethyl-alpha-[(tert-butylamino)methyl]benzyl alcohol from metered dose inhaler was being administered and the technician performing the pulmonary function tests which method or drug was being tested. The effect of one puff of 5-[1-hydroxy-2-[(1-methylethyl)amino]ethyl]-benzene diol (650 ug) via the invention was compared with one puff of 5-[1-hydroxy-2-[(1-methylethyl)amino]ethyl]-benzene diol and one puff of 4-hydroxy-3-hydroxymethyl-alpha-[(tert-butylamino)methyl]benzyl alcohol (100 ug) delivered by a conventional metered dose inhaler. All patients had used a metered dose inhaler regularly and had been instructed in their administration at least several months previously. Shortly before the study, all received further training from one of the investigators and were given instructions developed by Newman et al ["Simple Instructions for Using Pressurized Aerosol Bronchodilators", J. Royal Soc. Med., Vol. 73, pp 776–779 (1980)]: to shake the canister, place the mouthpiece of the metered dose inhaler between the lips while exhaling to FRC, to release the metered dose inhaler while performing a slow, deep inspiration to total lung capacity and to breathold at this lung volume while counting to ten.

Respiratory Inductive Plethysmography was determined in the following manner. A detailed description of the DC-coupled respiratory inductive plethysmograph and its calibration (Respitrace®, Non-Invasive Monitoring Systems, Inc., Ardsley, NY) is being published by Chahda et al, ["Validation of Respiratory Inductive Plethysmography Utilizing Different Calibration Procedures", Amer. Rev. Respir. Dis. (in press)]. It consists of two coils of Teflon insulated wire sewn into elastic bands encircling the rib cage and the abdomen which are connected to an oscillator module. Changes in cross-sectional areas of the rib cage and abdomen compartments alter the self inductance of the coils and frequency of their oscillations, which after appropriate calibration, reflect tidal volume measured by spirometry. Assuming that the respiratory systems moves with two degrees of freedom, the device is calibrated using rib cage, abdomen, and spirometer volumes and the equation rib cage/spirometer + abdomen/spirometer = 1. The subject breathes into a spirometer in two body postures to produce differences in rib cage and abdominal contributions to tidal volume and the equation is solved, graphically. Validation of the calibration of respiratory inductive plethysmography is performed against simultaneous spirometry in the upright and supine positions and the mean ($\pm$SD) percentage deviation from spirometry in the patients was $4.1\pm2.4\%$ and $4.6\pm2.8\%$, respectively.

The signals from the respiratory inductive plethysmograph were recorded on a Z-80A based microprocessor system (Respicomp®, Respitrace Corp., Ardsley, NY) which sampled the signals at 20 points/sec. At the moment of actuation of the metered dose inhaler, an observer signalled the computer with an analog step voltage. Later, the recording was analyzed by a cursor program and the computer calculated the following parameters:

(1) change in lung volume from FRC to actuation of metered dose inhaler, (2) change in lung volume from actuation of metered dose inhaler to peak inhalation, (3) durations of (1) and (2) and the breathholding time until subsequent exhalation, (4) mean inspiratory flow rates from FRC to actuation and from actuation to peak inhalation.

Statistical differences among the three treatments for improvement in lung function were analyzed by a nested factorial design of Hicks et al, ["Nested and Nested Factorial Experiments", Fundamental Concepts in the Design of Experiments 2 Edition, (1973) Holt, Rinehart and Winston Inc., New York, pp. 188–203]. This took into account variation in baseline measurements between the study days. If significance was found, the data were further analyzed by Q statistics to define which of the treatments produced the greatest response. Paired t-tests were also performed to compare the effects of the three treatments at each time interval after bronchodilator. The bronchodilator results in patients with a good metered dose inhaler technique were compared to those with a poor technique using an unpaired t-test. The results were expressed as means $\pm$ standard error (X$\pm$S.E.)

The size distributions measured by the 6-stage cascade impactor were approximately log-normal, with 5-[1-hydroxy-2-[(1-methylethyl)amino]ethyl]-benzene diol having a mass median aerodynamic diameter of 4.9 (SD$\pm$0.8) um with geometric standard deviation of 2.1 and 4-hydroxy-3-hydroxymethyl-alpha-[(tert-butylamino)methyl]benzyl alcohol having a mass median aerodynamic diameter of 2.4 (SD$\pm$0.28) um with geometric standard deviation of 1.7.

The impaction loss from the metered dose inhaler on the surface of the oropharyngeal model was 43% for 5-[1-hydroxy-2-[(1-methylethyl)amino]ethyl]-benzene diol and 31% for 4-hydroxy-3-hydroxymethyl-alpha-[(tert-butylamino)methyl]benzyl alcohol. When the 5-[1-hydroxy-2-[(1-methylethyl)amino]ethyl]-benzene diol was delivered into the air bag of the aerosol delivery system of FIG. 12, 50% of the aerosol was recovered by flushing the bag five times with clean air, indicating the 41% of the aerosol was lost in the device of FIG. 12. When attached to the glass model, 6% of the 5-[1-hydroxy-2-[(1-methylethyl)amino]ethyl]-benzene diol aerosol from device of FIG. 12 was deposited on the model. Therefore, for 5-[1-hydroxy-2-[(1-methylethyl)amino]-ethyl]-benzene diol, 47% of the aerosol was lost combined with the glass model leaving potentially 53% to enter the airways.

Determination of the number of breaths for airway deposition of aerosol was obtained in four normal subjects and four patients with chronic bronchitis. In the normal subjects, the number of breaths at which 90% of the initial aerosol in the device of FIG. 12 was retained in the lung was 4.8 (SD±0.8), while in the patients with chronic bronchitis, it was 1.8 (SD±0.8). Thus, in the patients it was felt that one breath from the device of FIG. 12 followed by a second breath of rebreathing from the bag together with breathholding between breaths would provide optimal deposition of aerosol without significantly increasing alveolar carbon dioxide.

The response to bronchodilators ws analyzed with mean changes of pulmonary functions indices with the three treatments being shown in FIGS. 14–16. FIG. 14 shows the mean percent changes in $SG_{aw}$ after administration of the three drug treatments. $SG_{aw}$ increased greater than 70% with all three treatments but the response to 5-[1-hydroxy-2-[(1-methylethyl)amino]ethyl]-benzene diol via the device of FIG. 12 was at all times significantly greater than with 5-[1-hydroxy-2-[(1-methylethyl)amino]ethyl]-benzene diol or 4-hydroxy-3-hydroxymethyl-alpha-[(tertbutylamino)methyl]benzyl alcohol administered by metered dose inhaler (p less than 0.003). There was no significant difference between 4-hydroxy-3-hydroxymethyl-alpha-[(tert-butylamino)methyl]benzyl alcohol and 5-[1-hydroxy-2-[(1-methylethyl)amino]ethyl]-benzene diol delivered by metered dose inhaler with maximal increases in $SG_{aw}$ of 86±26% and 101±24%, respectively, compared to the maximal increase of 195±52% with 5-[1-hydroxy-2-[(1-methylethyl)amino]ethyl]-benzene diol delivered via the invention. Two hours after administration of bronchodilator, a fall from the maximal value of $SG_{aw}$ was observed with 4-hydroxy-3-hydroxymethyl-alpha-[(tert-butylamino)methyl]benzyl alcohol and 5-[1-hydroxy-2-[(1-methylethyl)amino]ethyl]-benzene diol whereas the response to 5-[1-hydroxy-2-[(1-methylethyl)amino]ethyl]-benzene diol via the device of FIG. 12 was still well maintained.

A greater increase in $FEV_1$ was more frequently observed with 5-[1-hydroxy-2-[(1-methylethyl)amino]ethyl]-benzene diol via the device of FIG. 12 compared to 4-hydroxy-3-hydroxymethyl-alpha-[(tert-butylamino)methyl]benzyl alcohol or 5-[1-hydroxy-2-[(1-methylethyl)amino]ethyl]-benzene diol (FIG. 15) and mean maximal increases were 47±13%, 24±8% and 22±8%, respectively, but these differences did not reach group statistical significance. Similarly, a greater increase in FVC was observed more frequently with 5-[1-hydroxy-2-[(1-methylethyl)amino]ethyl]-benzene diol via the device of FIG. 12 (as graphed in FIG. 16) than with 4-hydroxy-3-hydroxymethyl-alpha-[(tert-butylamino)methyl]benzyl alcohol or 5-[1-hydroxy-2-[(1-methylethyl)amino]ethyl]-benzene diol and the maximum increases were 36±11%, ·13±4% and 9±4%, respectively. A significant difference was observed 30 minutes after 5-[1-hydroxy-2-[(1-methylethyl)amino]ethyl]-benzene diol via the invention compared to conventional metered dose inhaler, 36±11% and 13±4%, respectively, (p less than 0.05). A reduction in FRC was observed with all treatments and was marginally greater with 5-[1-hydroxy-2-[(1-methylethyl)amino]ethyl]-benzene diol via the invention compared to the other treatments (p=0.054).

Metered dose inhaler technique was studied in the following manner: Although all patients were regular users of metered dose inhaler (12.6 years average duration of use), and had received retraining a few days before the study, few succeeded in operating the conventional metered dose inhaler in accordance with the instructions they had received. Four patients were unable to coordinate metered dose inhaler actuation with the period of inhalation. One patient inhaled approximately 1 liter and breathheld for 6 seconds before actuating the metered dose inhaler and then immediately exhaled. A second patient actuated the inhaler during the expiratory phase after a deep inspiration, and a third patient actuated it at peak inspiration of a tidal breath, exhaled and the took a prolonged deep inhalation. The fourth patient actuated the inhaler while expiring and then proceeded to take a deep inspiration. All of these patients were able to use the device of FIG. 12 without difficulty.

Among the six patients who succeeded in actuating the inhaler during inspiration, most actuated it after they had inhaled approximately 0.5 liter of air. Following actuation, the average inhalation volume was 2 liters with a breathhold pause of 14 seconds. There was considerable variation in inspiratory flow rates and in the six patients with good metered dose inhaler technique, the mean flow rates were 1.02±0.29 L/sec and 0.54±0.16 L/sec during inhalation of 4-hydroxy-3-hydroxymethyl-alpha-[(tert-butylamino)methyl]benzyl alcohol and 5-[1-hydroxy-2-[(1-methylethyl)amino]ethyl]-benzene diol, respectively, compared to 0.19±0.02 L/sec and 0.24±0.03 L/sec during the first and second inhalations, respectively in all ten patients while using the device of FIG. 12. The highest inspiratory flow rate with the device of FIG. 12 was 0.50 L/sec compared to 1.90 L/sec with conventional metered dose inhaler.

A distinct difference was noted in the bronchodilator response to conventional metered dose inhaler administration between the patients with good technique defined as actuation of metered dose inhaler during inspiration irrespective of flow rate in contrast to poor technique defined as actuation of metered dose inhaler during breathholding or exhalation. The maximal increase in $SG_{aw}$ after 5-[1-hydroxy-2-[(1-methylethyl)amino]ethyl]-benzene diol via metered dose inhaler was 150±23% in the six patients with a good technique compared to 27±9.3% in the four with a poor technique (p less than 0.005). When the latter used the invention, three showed a maximal average increase in $SG_{aw}$ of 163±90% and one response comparable to that with conventional metered dose inhaler. Among the six patients with good metered dose inhaler technique the maximal response of $SG_{aw}$ to the device of FIG. 12 of 236±78% was considerably higher than the maximal response of 150±23% with metered dose inhaler delivering 5-[1-hydroxy-2-[(1-methylethyl)amino]ethyl]-benzene diol.

FIG. 13 illustrates a further embodiment of the invention. This embodiment has structure that enables it to be used for inhalation through the nose, allowing the nasal passages to be coated with the desired drug. The embodiment of FIG. 13 employs the basic nebulizer assembly 56 as shown in FIG. 12 with piece 19 and pressurized inhaler bottle 21. Mask 45 is provided for the patient with soft gasket 46 to improve sealing of the mask from outside air. Although mask 45, as shown, is applied by the patient over his nose and mouth, it is also contemplated that a mask could be used which is applied only over the nose of the patient. Mask 45 has aperture 48 located on the bottom portion thereof for the communication of the drug into the mask. Tube 47 connects aperture 48 of mask 45 to piece 19 of nebulizer assembly 56. Tube 47 may be made of a pliable plastic or other suitable material for securing around piece 19. Any other type of connection between tube 47 and mouthpiece 19 as would be known of by one ordinary skill in the art is also contemplated by this description. Nebulizer assembly 56 attaches to mounting portion 57 of airbag assembly 50. Airbag assembly 50 is comprised of apertured end cap 51 and end cap 52 connected together by sidewalls 53. Apertured end cap 51, end cap 52, and sidewalls 53 form cavity 54. Apertured end cap 51 and end cap 52 may be made of commercially available plastic material. It is contemplated that walls 53 are made of 2¼ mil polyethylene, although they may be composed of any suitably flexible and light material. Side walls 53 would be connected to apertured end cap 51 and end cap 52 by heat-sealing around the peripheries 58 thereof. The design of air bag assembly 54 can be of any suitable materials such that it provides a gas impermeable closed bag that may be attached to nebulizer assembly 56. It is particularly contemplated that the apertured end cap and the end cap may be manufactured in such a manner that it is easily portable and may fit in the pocket of any user. When apertured end cap 51 is detached from nebulizer assembly 56 with a twisting motion, apertured end cap 51 may be rotated in relation to end cap 52 to form a flat assembly with the side walls 53 automatically folded up therebetween. In addition, nebulizer 56 may be detached from mask 45 and tube 47 and these pieces may also be fit into the patient's pocket. These pieces, working in concert, provide for an easily assembled and easily used, highly effective apparatus.

The drug delivery device of the invention offers distinct advantages over the prior art drug delivery systems where the drug is "puffed" from a conventional inhaler, such as the pressured dosage inhalers that are used for 5-[1-hydroxy-2-[(1-methylethyl)amino]ethyl]-benzene diol and 4-hydroxy-3-hydroxymethyl-alpha-[(tert-butylamino)methyl]benzyl alcohol of the prior art of Boehringer Ingelheim and Shering (or Glaxo), respectively. When compared with the spacer systems that have been proposed, the airbag system embodied in the invention has distinct advantages. The airbag system compares favorably in terms of a minimal patient coordination being needed during the administration of the drug. The signal means of the invention provides for patient awareness of the flow rate and volume of air during administration of the drug, a further advantage over the spacer system that has been proposed. Reproducible dosing of the drug through a metered puff of the drug into the airbag is also an advantage of the invention particularly over the conventional inhalers that have been proposed for 5-[1-hydroxy-2-[(1-methylethyl)amino]ethyl]-benzene diol and 4-hydroxy-3-hydroxymethyl-alpha-[(tert-butylamino)methyl]benzyl alcohol in the prior art. A further advantage over both the inhalers for 5-[1-hydroxy-2-[(1-methylethyl)amino]ethyl]-benzene diol and 4-hydroxy-3-hydroxymethyl-alpha-[(tert-butylamino)methyl]benzyl alcohol as well as the spacers that have been proposed is the more even distribution of the drug throughout the inhalation maneuver by the patient. Conservation of medication through the more efficient distribution of the drug is a further advantage of the airbag system of the invention.

In particular, the ease of use by the patient is particularly important, minimal demands being placed on the patient for routine use of the airbag system of the invention, a point which is underscored by the studies mentioned in discussion of the background of the invention which show that many patients for even conventional 5-[1-hydroxy-2-[(1-methylethyl)amino]ethyl]-benzene diol and 4-hydroxy-3-hydroxymethyl-alpha-[(tert-butylamino)methyl]benzyl alcohol inhalers fail to properly use the systems. The signal means, preferably the reed whistle embodied in a preferred aspect of the invention, "trains" the patient on proper breathing techniques for the administration of the drug, and of course provides a built-in aid to signal the patient when he has exceeded the desirable maximum amount of air flow rate; in this manner, the patient learns how to perform the slow inspiratory flow maneuver and the magnitude of the "deep breath" that is advantageously taken for the administration of pulmonary medications. Minimization of the deposition of aerosol in the oropharynx is another consequence of the use of the invention with the controlled delivery of the drug from the airflow from the airbag, vis a vis the "puff" of drug with an inhaler for 5-[1-hydroxy-2-[(1-methylethyl)amino]ethyl]-benzene diol or 4-hydroxy-3-hydroxymethyl-alpha-[(tert-butylamino)methyl]benzyl alcohol that provides too much of the drug at one time. Reproducible dosing to the tracheobronchial tree is similarly maximized. To provide an even distribution in the tracheobronchial tree it is advantageous that there should be even distribution of the medication throughout the inhalation maneuver. Quite apart from the simplicity of construction and portability of the device of the invention and the other advantages noted above, it is to be particularly recognized that with the drug delivery device of the invention, a more effective drug administration is promoted than with 5-[1-hydroxy-2-[(1-methylethyl)amino]ethyl]-benzene diol or 4-hydroxy-3-hydroxymethyl-alpha-[(tert-butylamino)methyl]benzyl alcohol inhalers now on the market, with a minimization of drug being introduced into the system of the patient other than through the desired tracheobronchial tree.

The volume of the airbag for delivery of drug to the tracheobronchial tree via the mouth is typically 700 cc when the airbag is in its fully expanded state, although variations of from about 500 cc to about 1500 cc may be used in preferred aspects of the invention. A relatively smaller volume should be used for delivery to the nasal mucous passages, with 100 cc being a suitable maximum expanded volume for an airbag adapted for this use. The smaller volume provides a sufficient quantity of air to force the drug through the entire mucous membrane area of the nose, substantially more air providing for the propulsion of the contents of the airbag further into the patient, which in one embodiment of the invention (where delivery only to the nasal passages is desired) should be avoided. It is to be understood that if the drug is to be delivered beyond the nasal passages that a larger maximum air capacity for the airbag may be used, although in such applications it is to be understood that the drug will generally be delivered through the mouth.

With respect to rate of air that is used to trigger the signal means, those skilled in the art will understand that the rate at which the signal is triggered may be varied dependent upon the desired rate. In the invention for delivery of 5-[1-hydroxy-2-[(1-methylethyl)amino]ethyl]-benzene diol, it is desired to have the signal triggered with an inspiratory flow rate which exceeds 20 L/min, as one embodiment of this invention. A reed whistle is typically placed in the bidirectional channel so that as air is inhaled at a rate greater than 20 L/min, an audible whistling sound is emitted, thereby signalling the patient to slow down his rate of air intake, thereby avoiding too great a rate of intake and the attendant previously mentioned disadvantages.

In experiments conducted with a drug delivery device in accordance with the invention it was observed that virtually all of the loss of aerosol by impaction occurs in the airbag with none in the glass oropharyngeal model, demonstrating the superiority of the invention in terms of avoidance of medication entering the patient's system other than through the tracheobronchial tree. The extent of aerosol loss in the bag is similar to loss in the model when metered aerosol is directed into the model. Studies on aerosol retention in normal and bronchitic subjects who rebreathed 2.5 um mass median aerodynamic diameter aerosol of di-2-ethylhexyl sebacate from a 0.5 L reservoir bag at 10 breaths per minute. A discussion of measurements of this type for the invention is made in Brown et al, "Measurement of Aerosol Retention Using a Rebreathing Technique in Normal and Chronic Brochitics", in publication for *Am. Rev. Resp. Dis.* (in press). In normal subjects, 90% retention occurred at 4.6, SD 0.7 breaths and in brochitics 3.2, SD 0.7 breaths (p less than 0.01). Preliminary data in bronchitics indicate that 90% retention of aerosols of mass median aerodynamic diameter 4 um (size of metered aerosol particles) ought to occur within 2 breaths. Apart from drug loss in the airbag, the drug delivery device of the invention provides superior delivery of oronasally delivered drugs in comparison with known devices of the prior art such as the conventional inhalers for 5-[1-hydroxy-2-[(1-methylethyl)amino]ethyl]-benzene diol and 4-hydroxy-3-hydroxymethyl-alpha-[(tert-butylamino)methyl]benzyl alcohol, and share in common with such inhalers a simplicity of construction and economy of manufacture to make their routine use simple for patients who are able to carry the collapsed airbag in a small pocket pouch and instantly assemble the airbag and piece for use when required even outside the home.

In accordance with a further aspect of the present invention the compound 6alpha-flouro-11beta,16alpha,17,21-tetrahydroxypregna-1,4-diene-3,20-dione cyclic 16,17-acetal may be used as an agent for the treatment of bronchial asthma when administered via the tracheobronchial tree via a mouthpiece such as shown in FIG. 12. The drug is administered to the patient in the same manner as in FIG. 12, and provides relief from bronchial asthma. The drug 6alpha-flouro-11beta,16alpha,17,21-tetrahydroxypregna-1,4-diene-3,20-dione cyclic 16,17-acetal is presently known for a different application via nasal administration under the trademark Nasalide (Syntex Laboratories, Inc., Palo Alto, Calif.). When 6alpha-flouro-11beta,16alpha,17,21-tetrahydroxypregna-1,4-diene-3,20-dione cyclic 16,17-acetal is administered via the mouth to the tracheobronchial tree for relief from bronchial asthma in accordance with the present invention, a spray of Nasalide may be used for introduction into the airbag in accordance with FIG. 12. One puff (30 mcg) of Nasalide is contemplated as a dosage to be administered two times per day as one embodiment of the present invention as a treatment for bronchial asthma.

Figure 13:
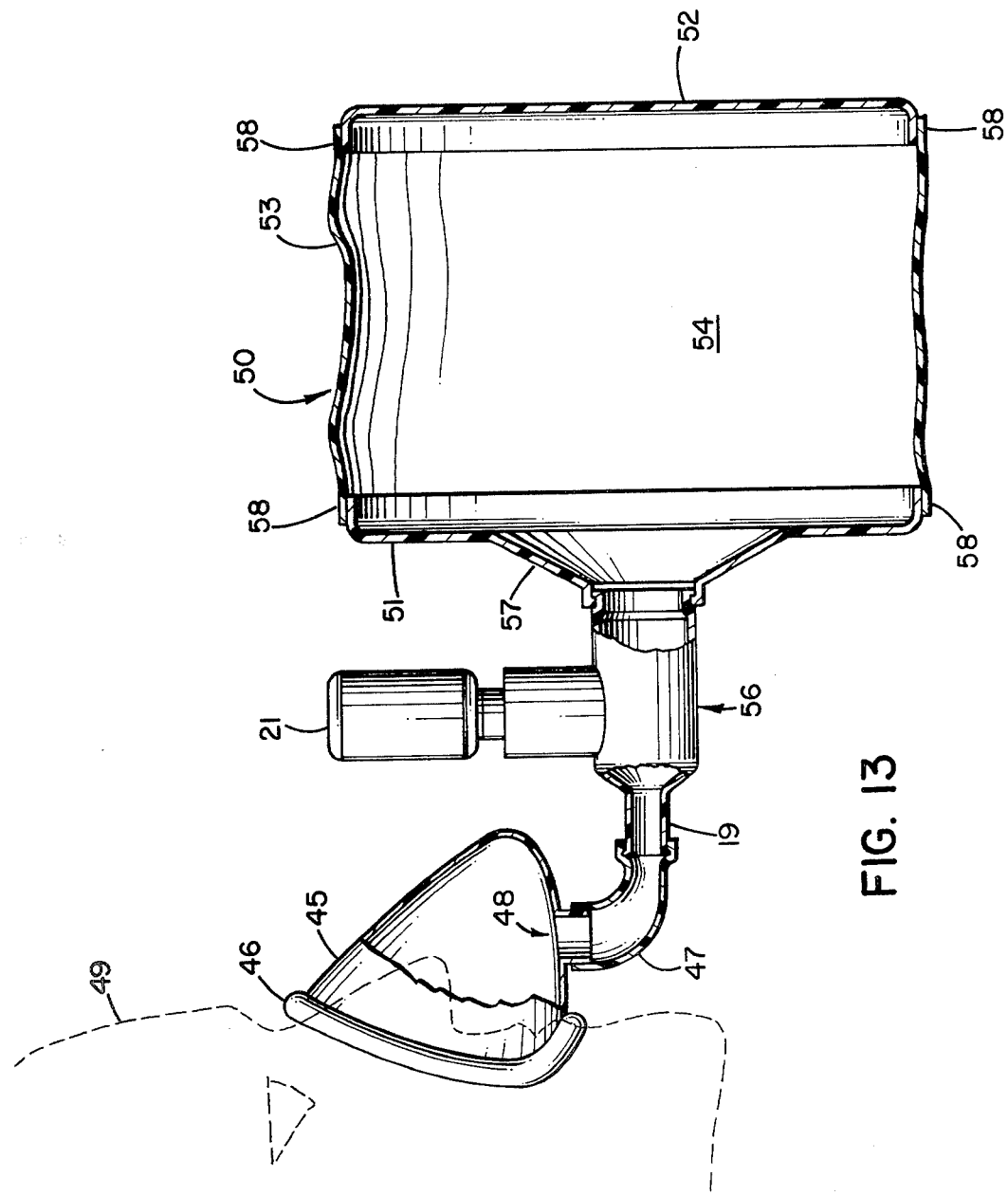
FIG. 13 is a cutaway, partial cross sectional view of the embodiment of the invention as shown in FIG. 12, but modified for use for the nasal delivery of drugs.
Figure 14:
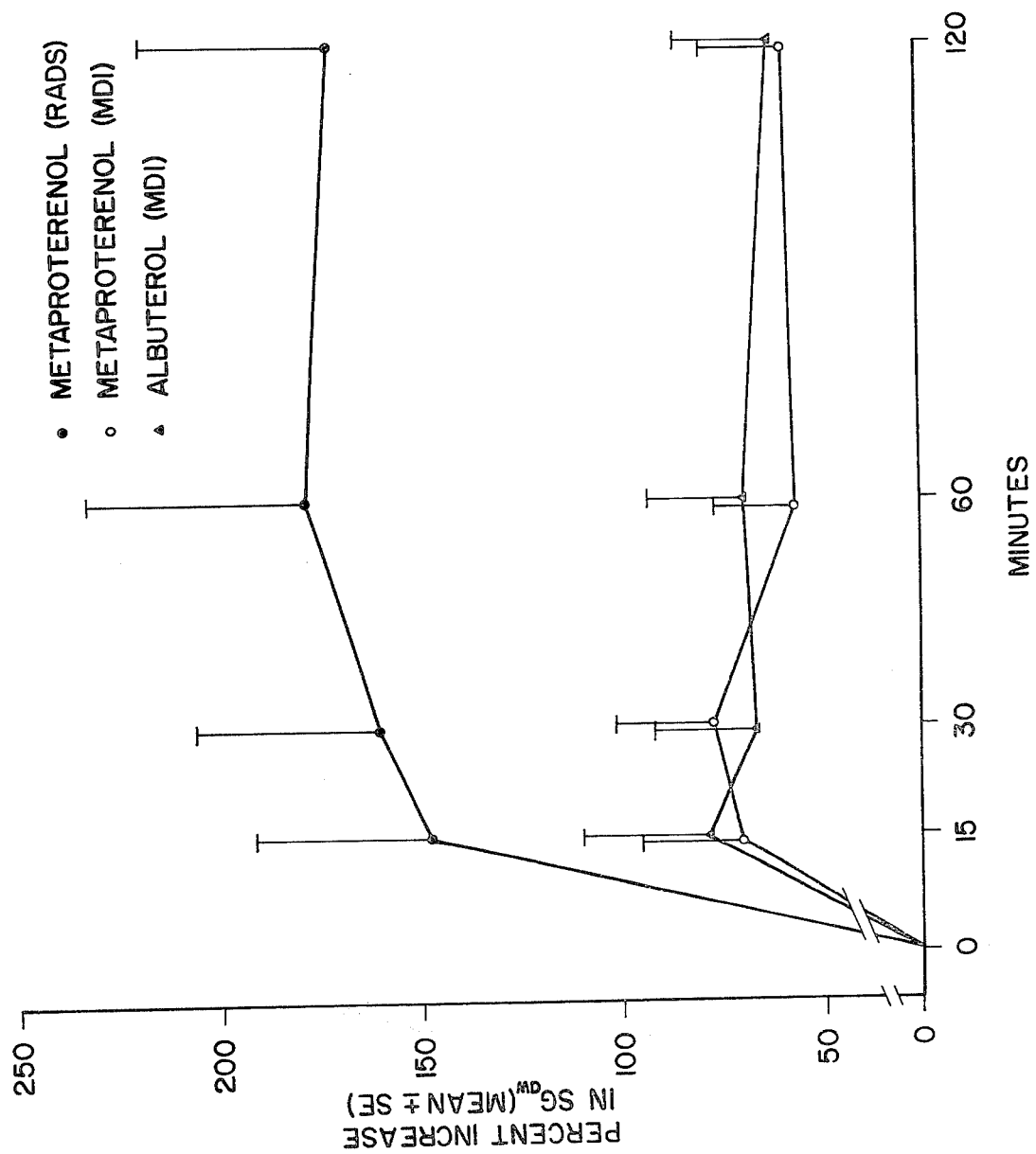
FIGS. 14–16 show the mean changes of pulmonary function indices with three treatments.
Figure 15:
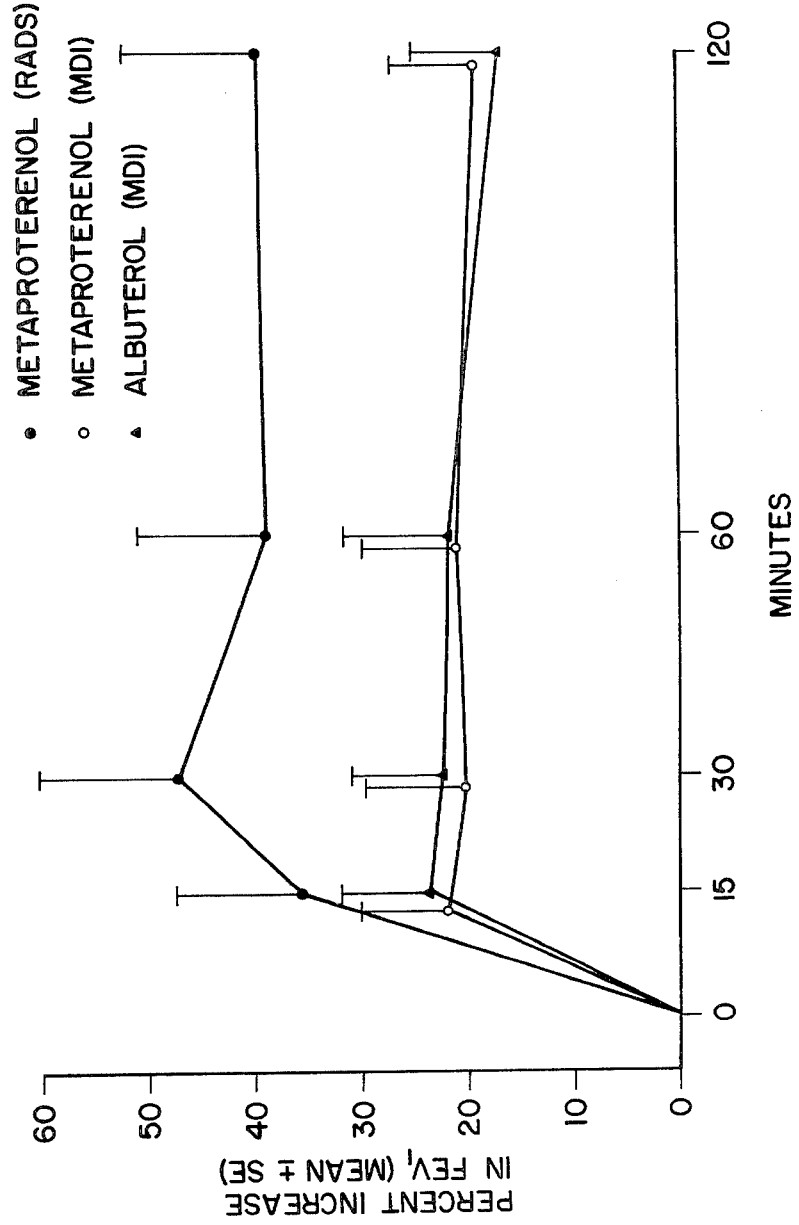
Figure 16:
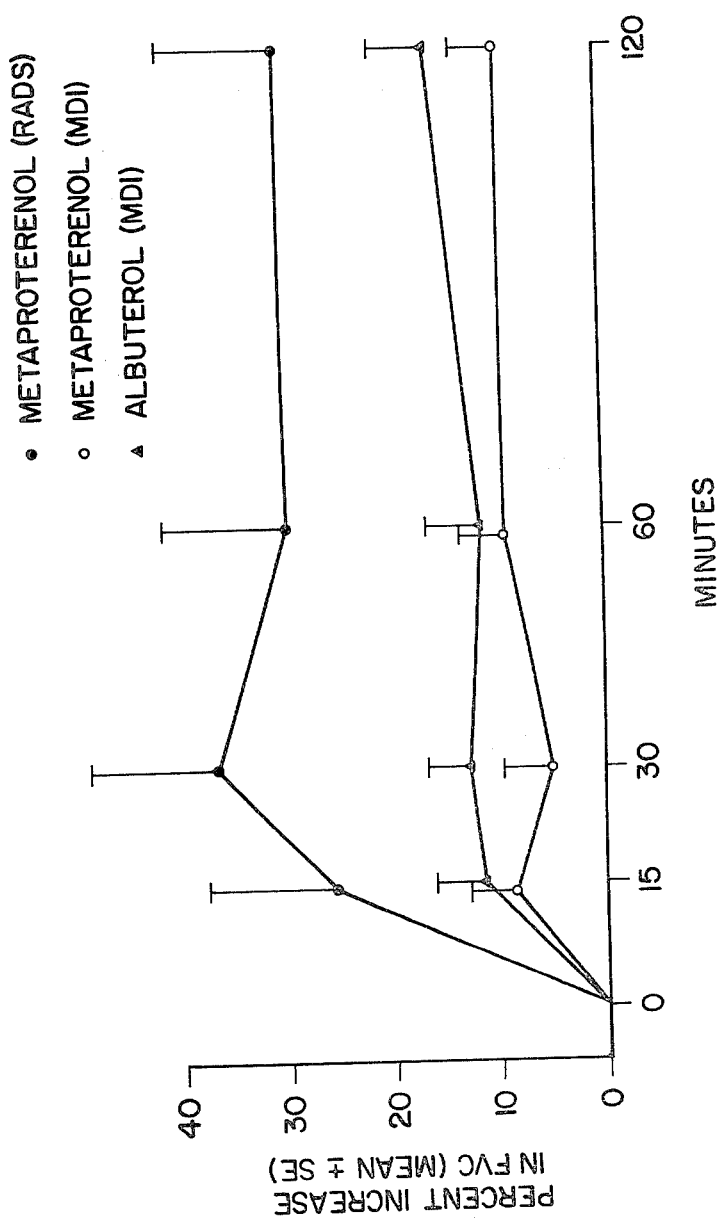

In accordance with a still further aspect of the present invention, it is contemplated that the compound 6alpha-flouro11beta,16alpha,17,21-tetrahydroxypregna-1,4-diene-3,20-dione cyclic 16,17-acetal may be used for allergic rhinitis when administered nasally in accordance with the embodiment of FIG. 13. The use of 6alpha-flouro-11beta,16alpha,17,21-tetrahydroxypregna-1,4-diene-3,20-dione cyclic 16,17-acetal for the treatment of allergic rhinitis is known from the commercial use of Nasalide which is nasally administered. Just as nasal administration set forth for the embodiment of FIG. 13 provides for a more even distribution of the drug to the nasal mucous passages while minimizing the entry of the drug into the system of the patient through other means, so too is this advantage to be obtained in for the administration of 6alpha-flouro-11beta,16alpha,17,21-tetrahydroxypregna-1,4-diene-3,20-dione cyclic 16,17-acetal. It is contemplated that with a spray of Nasalide one puff (30 mcg) delivered twice a day should be administered in accordance as one embodiment of this aspect of the present invention.

It should be noted that the airbag of the present invention is described as being "impervious" to the passage of drug. It is to be understood that materials such as polyethylene which are contemplated as a material for the airbag of the present invention permit the passage of drug molecules at a relatively slow rate used, for example, as solubility membranes for transdermal drug delivery systems. It is therefore to be understood that by "impervious" is contemplated materials which are substantially impervious to the passage of drug molecules for use in the invention where the drug only briefly contacts the airbag, polyethylene and other such materals being within the scope of the invention as materials suitable for the construction of the airbag. It is also to be appreciated that in an embodiment of the invention it is contemplated that an airbag material that would be substantially impervious to the passage of drug but which could permit passage of air therethrough could advantageously be used in the present invention, although currently there is no practical material that would satisfy this particular aspect of the present invention.

Figure 17:
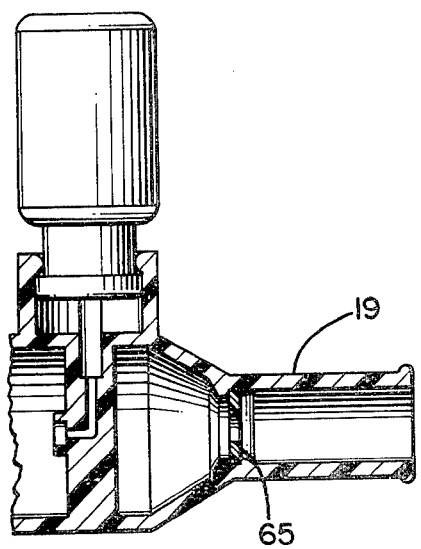
FIG. 17 is a side view of a portion of the drug delivery device of the invention containing a resistor means to control air flow.
Figure 18:
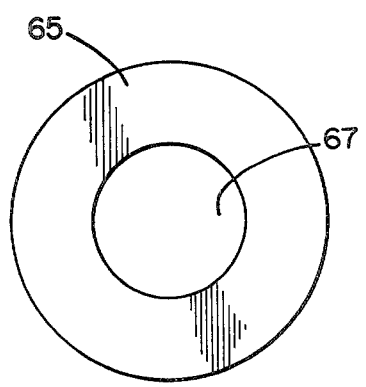
FIG. 18 is a front view of the resistor means shown in FIG. 17.

It is also to be noted that for some patients a signal means such as the reed whistle may not prove satisfactory, which is particularly the case with pediatric and geriatric patients. Children are less likely to obey the "command" of the whistle, either through lack of understanding or a general lack of discipline in following a doctor's instructions that would be expected in an adult. Geriatric patients often encounter a hearing problem. Accordingly, the airbag of FIG. 12 may be modified to include within the said bidirectional channel an air resistor means whereby even with great efforts on the part of the patient it is not readily possible to exceed a certain maximum airflow passage through the said bidirectional channel, i.e., a certain maximum airflow that would otherwise be controlled by the signal means could be the built-in maximum airflow for said bidirectional channel by virtue of inclusion in that bidirectional channel of a resistor means. As a resistor means illustrated in FIG. 17 (which shows only a portion of the mouthpiece of the embodiment of FIG. 12) there is included a washer-shaped disc 65, the amount of air which may pass through said bidirectional channel being restricted by the the washer-shaped disc 65 having orifice 67. The washer-shaped disc 65 is also shown in FIG. 18. In addition to the washer-shaped disc 65 other resistor means include a screen member 66 having frame 68 with screen 69 stretched across frame 68 shown in FIG. 19 which is substituted for the washer-shaped disc 65 in the configuration otherwise in accordance with FIG. 18. As an alternative to the resistor means which are found in FIGS. 18 and 19, and other obstruction within the bidirectional channel which will decrease the amount of air which may pass through said bidirectional channel per unit time may be substituted therefor, or a portion or all of the bidirectional channel between the point at which the drug enters the airbag to the point of communication with the mouth may have a narrower cross-sectional area than the area of the bidirectional channel between the point of entry of the aerosolized drug and the airbag.

Figure 19:
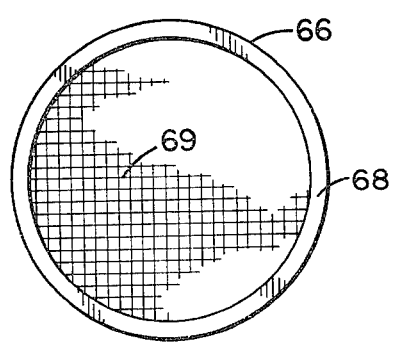
FIG. 19 is a front view of another resistor means useful in the drug delivery device of the invention.

In a further embodiment of the invention where it is desired to have very minute particles administered to the tracheobronchial tree, a screen may be used such as shown in FIG. 19 which only admits very small particles. For example, in the case of gram negative pneumonia, it is desirable to treat the deepest reaches of the lung with the active agent, for example, gentimicin sulfate. If the spray of the drug has large particles, the larger particles will "hit" the tracheobronchial tree at points before reaching the deep areas of the lung. By providing a screen that permits passage of only small particles, e.g., having a diameter less than about 0.1 micron, the patient will receive a drug spray where a significant portion of the drug will reach the desired deepest reaches of the lung. In one embodiment of this aspect of the invention where gentimycin sulfate is the drug used for treatment of gram negative pneumonia, a typical dosage would be 60 mg of the drug in an aerosolized puff through the device of FIG. 12, modified with a screen permitting passage only of particles having a diameter of less than 0.1 microns as modified in accordance with FIG. 19.

What is claimed is:

1. A method of administering a drug through a patient's breathing passage for absorption on the mucous tissue of the patient which comprises:
   (a) introducing a aerosol containing a predetermined amount of said drug into an expanded collapsible bag of fixed maximum dimension having means for communicating the aerosolized drug with a breathing passage of the patient and being otherwise substantially impervious to the passage of air;
   (b) collapsing said expanded bag while said means for communicating with a breathing passage is in position to deliver said aerosolized drug into the breathing passage of the patient, wherein said collapsing of said expanded bag takes place through inhalation by said patient, and wherein said patient is given a signal when the maximum desired rate of inhalation is reached;
   whereby the predetermined dosage of said drug is delivered to said mucous tissue in a manner substantially without absorption of said drug via the gastrointestinal tract.

2. A method of claim 1, wherein said signal is a whistle housed in said means for communicating with a breathing passage which is activated by air passing through said whistle at a rate in excess of the desired rate for delivery of said drug.

3. A method of claim 1, wherein the breathing passage is the mouth.

4. A method of claim 3, wherein the drug is delivered for absorption on the tracheobronchial tree.

5. A method of claim 4 for the delivery of a pulmonary medicine.

6. A method of claim 5, wherein said pulmonary medicine is a bronchodilator.

7. A method of claim 6, wherein said bronchodilator is 5-[1-hydroxy-2-[(1-methylethyl)amino]ethyl]-benzene diol.

8. A method of claim 6, wherein said bronchodilator is 4-hydroxy-3-hydroxymethyl-alpha-[(tert-butylamino)methyl]benzyl alcohol.

9. A method of claim 1, wherein the breathing passage is the nose.

10. A method of claim 9, wherein the amount of drug which enters the system of the patient other than through the nasal mucous membranes is minimized by said patient and maximum contact with the nasal mucous tissue is enhanced, further comprising the step, after said collapsing said expanded bag, of maintaining said means for communicating with a breathing passage in contact with the nose and then reexpanding said expanded bag, whereby the drug passes over the mucous tissues of the nasal passage a second time and the amount of drug which goes beyond the nasal passage for communication with the tracheobronchial or gastrointestinal routes is minimized.

11. A method of claim 9 or 10, wherein said drug is a nasal decongestant.

12. A method of claim 9 or 10, wherein said drug is 5-[1-hydroxy-2-[(1-methylethyl)amino]ethyl]-benzene diol.

13. A method of claim 9 or 10, wherein said drug is 4-hydroxy-3-hydroxymethyl-alpha-[(tert-butylamino)-methyl]benzyl alcohol.

14. A method of claim 9 or 10, wherein said drug is a systemically active drug.

15. A drug delivery device for administering a drug contained in an aerosol to a breathing passage of a patient for absorption on the mucous tissue of the patient which comprises
   (a) a collapsible airbag of fixed maximum dimensions which is impervious to passage of air except for an airbag opening;
   (b) a piece having one end adapted for communication with the breathing passage and connected by a bidirectional channel through said piece to the opposite end thereof to said airbag opening, said piece having a drug introduction opening for the introduction of an aerosol spray containing a predetermined amount of a drug, said drug introduction opening disposed such that said aerosol spray is introduced directly into said airbag through said piece and said airbag opening, in a direction away from said one end; and
   (c) signal means in said bidirectional channel to indicate when the rate of inhalation of said aerosol spray from said airbag exceeds a desirable limit, whereby the patient taking said drug is reminded to decrease the rate of collapse of said airbag, thereby maximizing drug utilization;
said drug delivery device admitting a drug-containing aerosol through said drug introduction opening while said collapsible airbag is at least partially expanded, said drug being introduced into said the breathing passage with the contraction of said collapsible airbag through inhalation by said patient.

16. A drug delivery device of claim 15, wherein said signal means is a whistle activated by passage of air from said airbag into said bidirectional channel at a rate in excess of the desirable limit for effective drug utilization.

17. A drug delivery device of claim 16, wherein said whistle is a reed.

18. A drug delivery device of claim 16, wherein said piece is a mask adapted for communication with the nose, whereby said drug is delivered to the nasal mucous membranes.

19. A drug delivery device of claim 15, wherein said piece is a tube adapted for communication with the mouth, whereby said drug is delivered to the tracheobronchial tree.

20. A drug delivery device of claim 19, wherein said collapsible bag has a first apertured end cap having said airbag opening and a second end cap facing said first apertured end cap, said two end caps being connected by a collapsible material.

21. A drug delivery device of claim 20, wherein said collapsible material is attached to said two end caps and is adapted such that as said airbag collapses, the facing end caps rotate in relation to each other.

22. A drug delivery device of claim 16, 17, 19, 20 or 21, wherein said drug is a bronchodilator.

23. A drug delivery device of claim 16, 17, 19, 20 or 21, wherein said drug is 5-[1-hydroxy-2-[(1-methylethyl)amino]-ethyl]-benzene diol.

24. A drug delivery of claim 16, 17, 19, 20 or 21, wherein said drug is 4-hydroxy-3-hydroxymethyl-alpha-[(tert-butylamino)methyl]benzyl alcohol.

* * * * *